(12) United States Patent
Li et al.

(10) Patent No.: US 10,326,077 B2
(45) Date of Patent: Jun. 18, 2019

(54) SOLUBLE GRAPHENE NANOSTRUCTURES AND ASSEMBLIES THEREFROM

(71) Applicant: Indiana University Research and Technology Corporation, Indianapolis, IN (US)

(72) Inventors: Liang-shi Li, Bloomington, IN (US); Xin Yan, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 30 days.

(21) Appl. No.: 15/198,013

(22) Filed: Jun. 30, 2016

(65) Prior Publication Data

US 2016/0308134 A1    Oct. 20, 2016

Related U.S. Application Data

(62) Division of application No. 13/520,735, filed as application No. PCT/US2011/020501 on Jan. 7, 2011, now Pat. No. 9,410,040.

(Continued)

(51) Int. Cl.
*H01B 1/04*     (2006.01)
*B82Y 30/00*    (2011.01)
(Continued)

(52) U.S. Cl.
CPC ........ *H01L 51/0045* (2013.01); *C01B 32/182* (2017.08); *C07C 13/62* (2013.01); *C07C 43/205* (2013.01); *C07C 63/44* (2013.01); *C07C 63/46* (2013.01); *C07C 69/78* (2013.01); *C09C 1/44* (2013.01); *C09D 5/24* (2013.01); *C09D 5/32* (2013.01); *B82Y 30/00* (2013.01); *B82Y 40/00* (2013.01); *C01P 2002/82* (2013.01); *C01P 2002/89* (2013.01); *C01P 2006/40* (2013.01); *C07C 2603/54* (2017.05); *H01L 51/0096* (2013.01); *H01L 51/44* (2013.01);
(Continued)

(58) Field of Classification Search
CPC .......... B82Y 30/00; C01B 32/194; H01B 1/04
USPC .......................... 252/510, 511; 977/758, 759
See application file for complete search history.

(56) References Cited

U.S. PATENT DOCUMENTS 6,506,928 B1    1/2003  Hirsch
2003/0001141 A1    1/2003  Sun et al.
(Continued)

FOREIGN PATENT DOCUMENTS

JP         2009151956         9/2009

OTHER PUBLICATIONS

Li "Dependence of Conductance of Corrugated Graphene Quantum Dot on Geometrical Features" Commun. Theor. Phys. 52 960 (Year: 2009).*

(Continued)

*Primary Examiner* — Tri V Nguyen
(74) *Attorney, Agent, or Firm* — Barnes & Thornburg LLP

(57) ABSTRACT

Disclosed herein is a method for preparing large soluble graphenes. The method comprises attaching one or more hindering groups to the graphene, which can prevent face-to-face graphene stacking by reducing the effects of inter-graphene attraction. The large graphenes can absorb a wide spectrum of light from UV to near infrared, and are useful in photovoltaic devices and sensitizers in nanocrystalline solar cells.

12 Claims, 10 Drawing Sheets

Related U.S. Application Data

(60) Provisional application No. 61/293,337, filed on Jan. 8, 2010.

(51) Int. Cl.

| | | |
|---|---|---|
| *H01L 51/00* | (2006.01) | |
| *C09C 1/44* | (2006.01) | |
| *C07C 13/62* | (2006.01) | |
| *C07C 43/205* | (2006.01) | |
| *C07C 63/44* | (2006.01) | |
| *C07C 63/46* | (2006.01) | |
| *C07C 69/78* | (2006.01) | |
| *C09D 5/24* | (2006.01) | |
| *C09D 5/32* | (2006.01) | |
| *C01B 32/182* | (2017.01) | |
| *B82Y 40/00* | (2011.01) | |
| *H01L 51/44* | (2006.01) | |

(52) U.S. Cl.
CPC ........ *Y10S 977/734* (2013.01); *Y10S 977/847* (2013.01); *Y10S 977/948* (2013.01); *Y10T 428/265* (2015.01)

(56) References Cited

U.S. PATENT DOCUMENTS

| | | |
|---|---|---|
| 2008/0221240 A1 | 9/2008 | Swager et al. |
| 2009/0029221 A1 | 1/2009 | Goddard et al. |
| 2009/0087493 A1 | 4/2009 | Dai et al. |
| 2009/0226361 A1 | 9/2009 | Campos-Delgado et al. |
| 2009/0324897 A1 | 12/2009 | Choi et al. |
| 2009/0325071 A1 | 12/2009 | Verbrugge et al. |
| 2010/0028681 A1* | 2/2010 | Dai ................. B82Y 30/00 428/408 |
| 2010/0105834 A1 | 4/2010 | Tour et al. |
| 2012/0272868 A1* | 11/2012 | Berry ............... B82Y 30/00 106/286.8 |

OTHER PUBLICATIONS

Berresheim et al., "Polyphenylene Nanostructures", Chem. Rev. 1999, 99, 1747-1785.

Simpson et al., "From graphite molecules to columnar superstructures—an exercise in Nanoscience". J. Mat. Chem. 2004, 14, 494-504.

Watson et al., "Big is Beautiful—"Aromaticity" revisited from the viewpoint of macromolecular and supramolecular enzene chemistry", Chem. Rev. 2001, 101, 1267-1300.

Wu et al., "Graphene as Potential Material for Electronics", Chem. Rev. 2007, 107, 718-747.

Muller et al., "Expanding Benzene to Giant Graphenes: Towards Molecular Devices", Phil. Trans. R. Soc. A 2007, 365, 1453-1472.

International Search Report and Written Opinion issued by the ISA/US in connection with PCT/US2011/020501 and completed on Mar. 30, 2011 (Mar. 30, 2011).

Bourlinos et al., "Surface Functionalized Carbogenic Quantum Dots." Small, 4, pp. 455-458, 2008.

Rao et al., "Graphene, the new nanocarbon." J Mater Chem, 19, pp. 2457-2469, web Jan. 20, 2009.

Si et al., "Synthesis of Water Soluble Graphene." NanoLetters, 8(6), p. 1479-1682, Web May 23, 2008.

Xu et al., "A Graphene Hybrid Material Covalently Functionalized with Porphyrin: Synthesis and Optical Limiting Property." Adv Materials, 21, p. 1275-1279, 2009.

\* cited by examiner

SOLUBLE GRAPHENE NANOSTRUCTURES AND ASSEMBLIES THEREFROM

CROSS-REFERENCE TO RELATED APPLICATIONS

This application is a divisional of U.S. Ser. No. 13/520,735 filed on Jul. 5, 2012, which is a U.S. national counterpart application of International Application Serial No. PCT/US2011/020501, filed Jan. 7, 2011 under 35 USC § 371, which claims priority under 35 USC § 119(e) to U.S. Provisional Application Ser. No. 61/293,337, filed on Jan. 8, 2010, the entire disclosures of which are incorporated herein by reference.

GOVERNMENT RIGHTS

This invention was made with government support under 0747751 awarded by the National Science Foundation. The Government has certain rights in the invention.

TECHNICAL FIELD

This invention relates generally to the carbon nanostructures that exhibit useful band-gaps and methods of manufacturing and using the same. More specifically, the invention relates generally to graphene quantum dots and methods of manufacturing and using the same.

SUMMARY

According to the present disclosure, a graphene nanostructure is described. Methods of preparing a graphene nanostructure, methods of forming graphene nanostructured assemblies, and graphene nanostructured assemblies are also described.

In illustrative embodiments, a composition comprises a population of graphene quantum dots. The quantum dots comprise nanostructured graphene, described simply as "graphene" herein, and an encapsulating means for solubilizing the graphene to prevent aggregation so that the population of graphene quantum dots remains solvated in solution. The encapsulating means is covalently linked to the graphene.

In further illustrative embodiments, a composition includes a population of graphene quantum dots, wherein a quantum dot comprises graphene, a solubilizing group and a binding group. In one embodiment, the graphene includes from about 100 to about 60000 conjugated atoms. For example, the graphene includes 100 to about 60000 conjugated carbon atoms. In illustrative embodiments, the graphene has a ribbon structure or a sheet structure. Furthermore, the quantum dot includes solubilizing groups, the solubilizing groups including a steric hindering group. In one embodiment, the steric hindering group includes a branching component and a bulking component. In another embodiment, the branching component and the bulking component are independently selected from an alkyl, alkenyl, alkynyl, cycloalkyl, heteroalkyl, or cycloheteroalkyl, each of which is optionally substituted. In another embodiment, the bulking component is derived from a natural plant oil, a natural animal oil, a semi-synthetic oil, a silicone oil, an ester oil, a higher alcohol, a dendrimer, or a hydrocarbon oil.

In illustrative embodiments, the quantum dot includes a binding group. The binding group is a chemical functional group having an attraction to an inorganic solid. In one embodiment, the binding group is a chemical functional group having an attraction to titanium dioxide. In another embodiment, the binding group is a carbonyl or derivative thereof, a carboxylate or derivative thereof, a sulfonyl or derivative thereof, a phosphinyl or derivative thereof, a phosphonyl or derivative thereof, a phosphate or derivative thereof, or an arsenate or a derivative thereof.

In further illustrative embodiments, a photovoltaic device comprises a population of solubilized quantum dots. In one embodiment, the photovoltaic device includes an inorganic substrate in contact with the quantum dots. In another embodiment, the inorganic substrate is titanium dioxide. In another embodiment, the inorganic substrate has a surface that can be approximated as a plane at nanoscale dimensions and quantum dot has a sheet-like structure; illustratively, the orientation of the sheet-like structure is non-parallel to the inorganic substrate's surface.

In illustrative embodiments, a nanostructure assembly of graphene quantum dots comprises an inorganic substrate and a population of graphene quantum dots, wherein (a) the graphene quantum dots have a sheet structure having a first face and a second face that is a monolayer in thickness, a length of from about 1 nanometer to about 4 nanometers and a width of from about 0.5 nanometers to about 5 nanometers, (b) the graphene quantum dots include a solubilizing group that is covalently bound to the edge of the sheet structure, and (c) the solubilizing group solubilizes and prevents aggregation of the graphene quantum dots extending from the edge in at least two directions to partially encapsulate the first face and the second face of the sheet structure. In one embodiment, the solubilizing group solubilizes and prevents aggregation of the graphene quantum dots extending from the edge in three directions, wherein the third direction is away from the graphene sheet structure. In another embodiment, the graphene quantum dots further comprising a binding group covalently bound to the edge of the sheet structure. In another embodiment, the binding group interacts with the inorganic substrate to cause the quantum dots to orient on the inorganic substrate so that the edge of the graphene quantum dot is in contact with inorganic surface, the first face and the second face oriented non-parallel to the inorganic surface.

In illustrative embodiments, a method of producing a soluble graphene quantum dot comprises oxidizing a solubilized polyphenylene dendrimeric precursor. In further, illustrative embodiments, a method for producing the quantum dots described herein is described.

DETAILED DESCRIPTION

Composition, size, and shape are parameters defining the properties of zero- and one-dimensional inorganic nanomaterials. In the case of graphenes, the geometry and chemical nature of the edges also play a role in determining the electronic and magnetic properties. Thus, to make graphene nanostructures with well-defined properties, it is important to achieve structural control with atomic precision.

One approach to achieve structural control is with solution chemistry; however, the rapidly decreasing solubility of graphenes with increasing size poses a tremendous challenge for the solution-chemistry approach to large graphene nanostructures. Large graphenes have a strong tendency to stack into insoluble graphite-like aggregates due to increasing inter-graphene attraction which may preclude well-defined chemical reactions and may prevent the purification of the reaction products.

One way to solubilize conjugated systems is lateral attachment of flexible side chains, and it has been successful for solubilizing small graphene molecules (Wu et al., Chem. Rev. 107, 718-747 (2007); Sakamoto et al., Angew. Chem. Intl. Ed. 48, 1030-1069 (2009)). The affinity between solvents and the flexible chains overcomes the inter-graphene attraction, resulting in the graphenes to be entropically pushed apart. However, since the maximum number of the flexible side chains and thus the chain-solvent interaction scales with perimeter of the graphenes (~$\alpha$, with $\alpha$ being the diameter) while the inter-graphene attraction scales with area (~$\alpha^2$), for graphenes with increasing size the inter-graphene attraction rapidly overtakes the solubilization forces, making such a strategy less and less effective.

Described herein is a solubilization strategy to overcome this problem by enclosing graphenes in three dimensions. Employing the strategy disclosed herein, large soluble graphene quantum dots have been obtained with atomic precision. The quantum dots absorb a wide spectrum of light from UV to near infrared, and are useful as a sensitizer in nanocrystalline solar cells.

Figure 1:
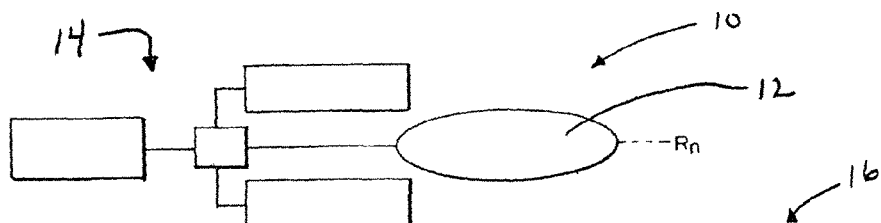
FIG. 1 is a diagrammatic representation of a first embodiment of a quantum dot comprising graphene and a first solubilizing group $R_1$ and showing that the quantum dot may optionally include additional solubilizing groups ($R_n$)

Referring now to FIG. 1, shown is a diagrammatic representation of a first embodiment of a quantum dot 10 comprising graphene 12 and a first solubilizing group 14 and showing that the quantum dot may optionally include additional solubilizing groups ($R_n$). In illustrative embodiments, graphene 12 may include from about 100 to about 60000 conjugated atoms. In one embodiment, graphene 12 has a ribbon structure having a monolayer thickness, a ribbon length, and a ribbon width, wherein the ribbon length is from about 2 nanometers to about 2 centimeters and the ribbon width is from about 0.5 nanometers to about 5 nanometers. In another embodiment, graphene 12 includes from about 100 to about 600 conjugated atoms. According to this embodiment, the graphene may have a sheet structure having a monolayer thickness, a sheet length, and a sheet width, wherein the sheet length is between about 1 nanometer and about 4 nanometers and the sheet width is from about 0.5 nanometers to about 5 nanometers. In another embodiment, the sheet width and the sheet length provide a sheet area of 3 square nanometers to about 20 square nanometers. In another embodiment, the conjugated atoms include (a) covalently-linked carbon atoms and (b) a system of p-orbitals populated with delocalized electrons, wherein the system of p-orbitals overlap with one another across an intervening sigma bond to bridge the sigma bond, and the delocalized electrons are associated collectively to the graphene.

Figure 2:
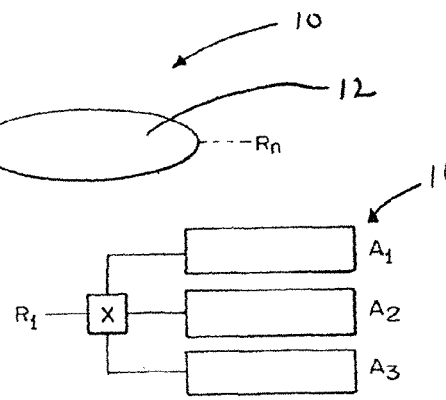
FIG. 2 is a diagrammatic representation of an embodiment of the solubilizing group showing a branching component (X) and bulking components $A_1$, $A_2$, and $A_3$.

In illustrative embodiments, the quantum dot includes an encapsulating means having a structure that provides one example of an encapsulating means. In one embodiment, the encapsulating means provides a steric hindering group covalently bound to the graphene. In another embodiment, the encapsulating means provides a solubilizing group covalently bound to the graphene. Referring now to FIG. 2, shown is a diagrammatic representation of an embodiment of a solubilizing group 16 showing a branching component (X) and bulking components $A_1$, $A_2$, and $A_3$. In one embodiment, the steric hindering group includes a branching component and a bulking component. In another embodiment, the steric hindering group includes one branching group and three bulking groups. In one embodiment, the branching component and the bulking component are independently selected from an alkyl, alkenyl, alkynyl, cycloalkyl, heteroalkyl, or cycloheteroalkyl, each of which is optionally substituted.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkenyl may also include one or more double bonds. It is to be further understood that in certain embodiments, alkyl is advantageously of limited length, including $C_4$-$C_{60}$, $C_6$-$C_{50}$, $C_8$-$C_{36}$, $C_{10}$-$C_{24}$, and $C_{12}$-$C_{20}$. It is to be further understood that in certain embodiments alkenyl and/or alkynyl may each be advantageously of limited length, including $C_4$-$C_{60}$, $C_6$-$C_{50}$, $C_8$-$C_{36}$, $C_{10}$-$C_{24}$, and $C_{12}$-$C_{20}$. It is appreciated herein that shorter alkyl, alkenyl, and/or alkynyl groups may provide less steric bulk and less solubilization capacity to the graphene and accordingly the graphene quantum dot will have different solution and surface-bound characteristics. Illustrative alkyl groups are, but not limited to n-butyl, isobutyl, sec-butyl, tert-butyl, pentyl, 2-pentyl, 3-pentyl, neopentyl, hexyl, heptyl, octyl, nonyl, decyl, undecyl, dodecyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_4$-$C_{60}$, $C_6$-$C_{50}$, $C_8$-$C_{36}$, $C_{10}$-$C_{24}$, and $C_{12}$-$C_{20}$. It is appreciated herein that shorter alkyl and/or alkenyl chains forming cycloalkyl and/or cycloalkenyl, respectively, may less steric bulk and less solubilization capacity to the graphene and accordingly the graphene quantum dot will have different solution and surface-bound characteristics.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like. As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

In an illustrative embodiment, the bulking component is derived from a natural plant oil, a natural animal oil, a semi-synthetic oil, a silicone oil, an ester oil, a higher alcohol, a dendrimer, or a hydrocarbon oil. As used herein, natural plant oils, animal oils, and semi-synthetic oils include avocado oil, linseed oil, almond oil, Ibota wax, perilla oil, olive oil, cacao butter, kapok wax, kaya oil, carnauba wax, Glycyrrhiza oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methylester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolate, hexyl laurate, POE lanolin alcohol ether, POE lanolin alcohol acetate, polyethylene glycol lanolate, POE hydrogenated lanolin alcohol ether, and egg yolk oil, wherein POE represents polyoxyethylene.

As used herein, hydrocarbon oils include ozokerite, squalane, squalene, ceresin, paraffin, paraffin wax, liquid paraffin, pristane, polyisobutylene, microcrystalline wax, and Vaseline. Examples of higher fatty acids include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid. As used herein, higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (cerakyl alcohol). As used herein, ester oils include diisobutyl adipate, 2-hexyldecyl adipate, di-2-heptylundecyl adipate, N-alkyl glycol mono isostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, isononyl isononanate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl. Examples of glyceride oils include acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristyl isostearate.

As used herein, silicone oils include linear organopolysiloxanes having a low viscosity to a high viscosity, such as dimethylpolysiloxane, methylphenylpolysiloxane, methylhydrogenpolysiloxane and a copolymer of dimethylsitoxane and methylphenylsiloxane, branched organopolysiloxane, cyclic siloxanes, such as octamethylcyclotetrasiloxane, decamethylcyclopentasiloxane, dodecamethylcyclohexasiloxane, tetramethyl-tetrahydrogencyclotetrasiloxane; silicone rubbers, such as gummy dimethylpolysiloxanes having high polymerization degrees and gummy dimethylsiloxane-methylphenylsiloxane copolymers having high polymerization degrees; and cyclosiloxane solutions of silicone rubber, trimethylsiloxysilicate, cyclosiloxane solutions of trimethylsiloxysilicate, higher alkoxy-modified silicones such as stearoxysilicone, higher fatty acid-modified silicones, alkyl-modified silicones, siliconols, fluorine-modified silicones, and solutions of silicone resins in a cyclic siloxane.

Figure 3:
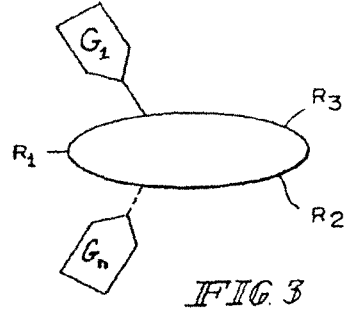
FIG. 3 is a diagrammatic representation of a second embodiment of a quantum dot comprising graphene and solubilizing groups $R_1$, $R_2$, and $R_3$ and showing a first binding group ($G_1$) and showing that the quantum dot may optionally include additional binding groups ($G_n$.

Referring now to FIG. 3, in other illustrative embodiments of a quantum dot comprising graphene and one or more solubilizing groups $R_1$, $R_2$, and $R_3$, the quantum dot further comprises a first binding group ($G_1$) and showing that the quantum dot may optionally include additional binding groups ($G_n$). In one embodiment, the binding group is a chemical functional group having an attraction to an inorganic solid. In another embodiment, the first binding group is a chemical functional group having an attraction to titanium dioxide. In another embodiment, the first binding group is a carbonyl or derivative thereof, a carboxylate or derivative thereof, a sulfonyl or derivative thereof, a phosphinyl or derivative thereof, a phosphonyl or derivative thereof, a phosphate or derivative thereof, or an arsenate or a derivative thereof.

As used herein, the term "carbonyl and derivatives thereof" includes the group C(O), C(S), C(NH) and substituted amino derivatives thereof. As used herein, the term "carboxylate and derivatives thereof" includes the group $CO_2H$ and salts thereof, and esters and amides thereof, and CN. As used herein, the term "sulfonyl or a derivative thereof" includes $SO_3H$ and salts thereof, and esters and amides thereof. As used herein, the term "phosphinyl or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted. As used herein, the term "phosphonyl or a derivative thereof" includes $PO_3H_2$ and salts thereof, and esters and amides thereof.

In illustrative embodiments, the quantum dot has formula, $Y-(R)_n$, wherein Y is a polycyclic aromatic group, $R_n$ is a first to an $n^{th}$ solubilizing group, wherein n is 1, 2, 3, 4, 5, or 6. In further illustrative embodiments, described is a composition of the formula, $(A)_m-Y-(R)_n$, wherein Y is a polycyclic aromatic group, $(R)_n$ is a first to an $n^{th}$ solubilizing group, $(A)_m$ is a first to an $m^{th}$ binding group, n is equal to 1, 2, 3, 4, 5, or 6, and m is equal to 1, 2, 3, 4, 5, or 6. In one embodiment, $(R)_n$ are independently selected from an alkyl, alkenyl, alkynyl, cycloalkyl, heteroalkyl, or cycloheteroalkyl, each of which is optionally substituted. In another embodiment, $(A)_m$ are independently selected from a carbonyl or derivatives thereof, a carboxylate or derivatives thereof, a sulfonyl or derivative thereof, a phosphinyl or derivative thereof, a phosphonyl or derivative thereof, a phosphate or derivative thereof, or an arsenate or a derivative thereof. In one embodiment, the polycyclic aromatic group has a molecular weight of from about 1200 g/mole to about 7200 g/mole.

Figure 4:
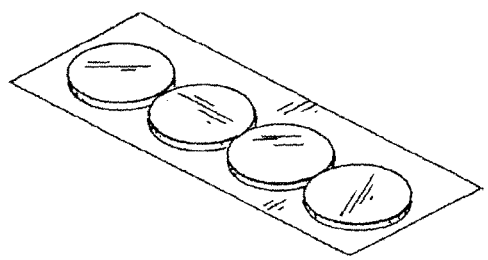
FIG. 4 is a perspective view of a diagrammatic representation of four quantum dots in contact with a inorganic surface showing that a face of each quantum dot is parallel and contacting the inorganic surface and showing a manner in which the four quantum dots may orient on the surface in relation to each other.
Figure 5:
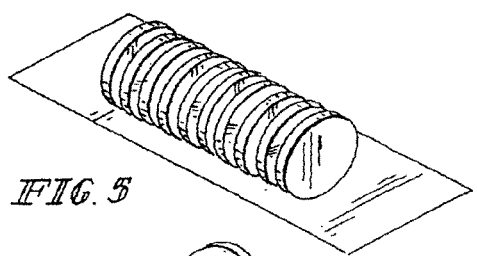
FIG. 5 is a perspective view of a diagrammatic representation of a plurality of quantum dots in contact with the inorganic surface showing that an edge of each quantum dot is contacting the inorganic surface orienting the face of each quantum dot non-parallel to the inorganic surface, further showing a manner in which the plurality of quantum dots may orient on the surface in relation to each other.
Figure 6:
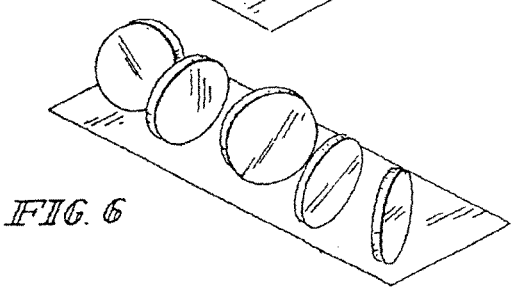
FIG. 6 is a perspective view of a diagrammatic representation of a plurality of quantum dots in contact with the inorganic surface showing that an edge of each quantum dot is contacting the inorganic surface orienting the face of each quantum dot non-parallel to the inorganic surface, further showing a manner in which the plurality of quantum dots may orient on the surface in relation to each other.

In illustrative embodiments, a photovoltaic device comprises the graphene quantum dot compositions described herein. In one embodiment, the photovoltaic device comprises graphene quantum dots contacting an inorganic substrate. In another embodiment, the inorganic substrate is titanium dioxide. Referring now to FIG. 4, one aspect of the present disclosure is that a manner of controlling the assembly of quantum dots on inorganic substrates was discovered. FIG. 4 is a perspective view of a diagrammatic representation of four quantum dots in contact with a inorganic surface showing that a face of each quantum dot is parallel and contacting the inorganic surface and showing a manner in which the four quantum dots may orient on the surface in relation to each other. Referring now to FIG. 5, shown is a perspective view of a diagrammatic representation of a plurality of quantum dots in contact with the inorganic surface showing that an edge of each quantum dot is contacting the inorganic surface orienting the face of each quantum dot non-parallel to the inorganic surface, further showing a manner in which the plurality of quantum dots may orient on the surface in relation to each other. Finally, FIG. 6 shows a perspective view of a diagrammatic representation of a plurality of quantum dots in contact with the inorganic surface showing that an edge of each quantum dot is contacting the inorganic surface orienting the face of each quantum dot non-parallel to the inorganic surface, further showing a manner in which the plurality of quantum dots may orient on the surface in relation to each other.

Figure 7:
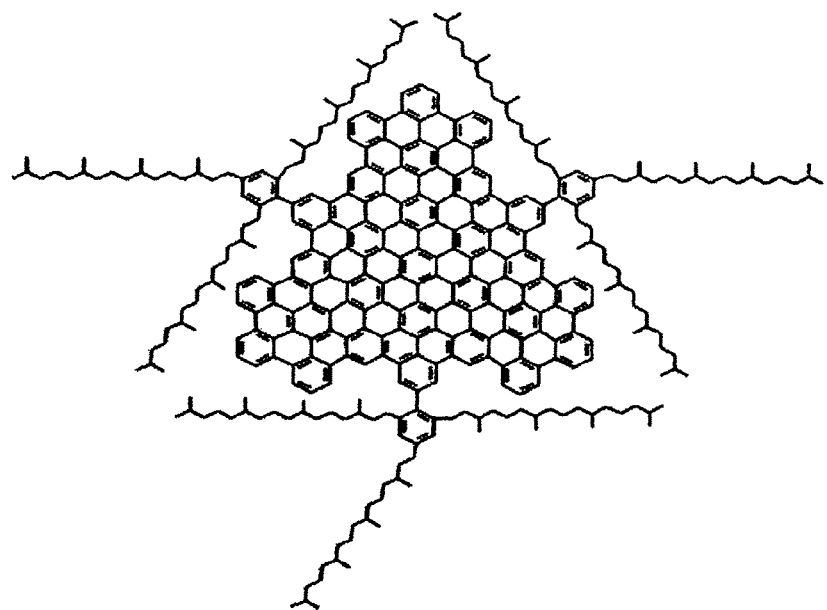
FIG. 7 is a structure for one embodiment showing the quantum dot with graphene having 168 conjugated carbon atoms, a tri-substituted phenyl branching component in each R position, and a $C_{20}$ bulking components in each A position.

It was discovered that the orientation of the graphene quantum dots on a surface can be controlled by varying the solubilizing groups and the binding groups. One aspect is that the solubilizing groups provide the solubilization so that the quantum dots do not aggregate and precipitate. However, these solubilization groups also influence the manner in which the quantum dots interact with a surface. Referring to FIG. 7, shown is a structure for one embodiment showing the quantum dot with graphene having 168 conjugated carbon atoms, a tri-substituted phenyl branching component in each R position, and a $C_{20}$ bulking components in each A position. It was discovered that this structure would exhibit assemblies like that shown in FIG. 4. However, a modified structure, such as that shown in FIG. 8, would assemble into a structure such as shown in FIG. 5 or FIG. 6. depending on the R groups selected for $R_1$ and $R_2$.

In illustrative embodiments, the inorganic substrate has a surface that can be approximated as a plane at nanoscale dimensions and the polycyclic aromatic group has a sheet-like structure, and wherein the composition is oriented on the inorganic substrate in a manner so that the sheet-like structure is non-parallel to the inorganic substrate planar surface. In further illustrative embodiments, a nanostructure assembly of graphene quantum dots comprising an inorganic substrate and a population of graphene quantum dots, wherein (a) the graphene quantum dots have a sheet structure having a first face and a second face that is a monolayer in thickness, a length of from about 1 nanometer to about 4 nanometers and a width of from about 0.5 nanometers to about 5 nanometers, (b) the graphene quantum dots include a solubilizing group that is covalently bound to the edge of the sheet structure, and (c) the solubilizing group solubilizes and prevents aggregation of the graphene quantum dots extending from the edge in at least two directions to partially encapsulate the first face and the second face of the sheet structure. In one embodiment, the solubilizing group solubilizes and prevents aggregation of the graphene dots extending from the edge in three directions, wherein the third direction is away from the graphene sheet structure. In another embodiment, the graphene quantum dots further comprising a binding group covalently bound to the edge of the sheet structure.

Figure 8:
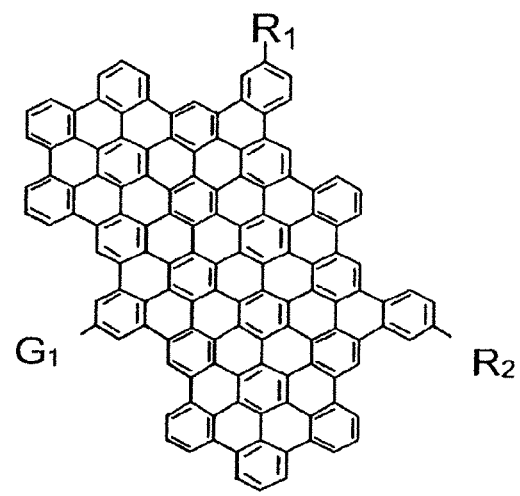
FIG. 8 is the structure for another embodiment showing the quantum dot with graphene having 132 conjugated carbon atoms, two solubilizing groups ($R_1$ and $R_2$), and coupling group ($G_1$)
Figure 9:
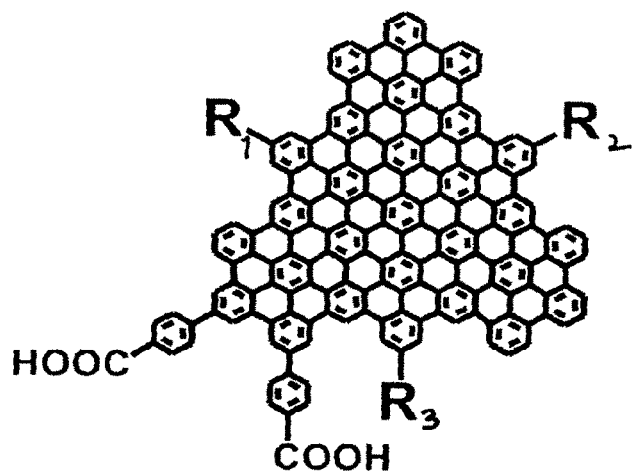
FIG. 9 is the structure for another embodiment showing the quantum dot with graphene having 132 conjugated carbon atoms, three solubilizing groups ($R_1$, $R_2$, and $R_3$), and two coupling group (shown as carboxylic acids)
Figure 10:
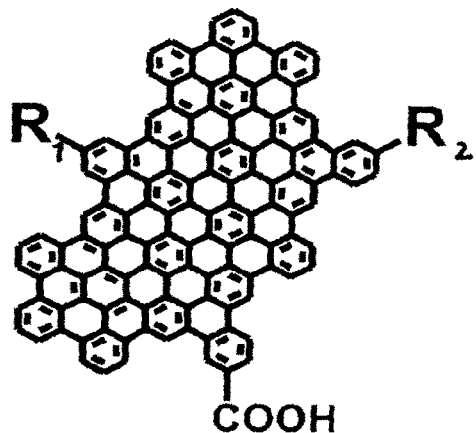
FIG. 10 is the structure for another embodiment showing the quantum dot with graphene having 132 conjugated carbon atoms, two solubilizing groups ($R_1$ and $R_2$), and a coupling group (shown as a carboxylic acid)

In illustrative embodiments, the binding group interacts with the inorganic substrate to cause the quantum dots to orient on the inorganic substrate so that the edge of the graphene quantum dot is in contact with inorganic surface, the first face and the second face oriented non-parallel to the inorganic surface. In one embodiment, the solubilizing group directs the population of quantum dots on the inorganic substrate to align so that the sheets are predominantly parallel (e.g. FIG. 5). In another embodiment, the solubilizing group directs the population of quantum dots on the inorganic substrate to not form an organized pattern (e.g. FIG. 6). Referring now to FIG. 8, shown is another structure for an embodiment showing the quantum dot with graphene having 168 conjugated carbon atoms, two solubilizing groups ($R_1$ and $R_2$), and coupling group ($G_1$). FIG. 9 is the structure for another embodiment showing the quantum dot with graphene having 132 conjugated carbon atoms, three solubilizing groups ($R_1$, $R_2$, and $R_3$), and two coupling group (shown as carboxylic acids). FIG. 10 is the structure for another embodiment showing the quantum dot with graphene having 132 conjugated carbon atoms, two solubilizing groups ($R_1$ and $R_2$), and a coupling group (shown as a carboxylic acid).

Figure 11:
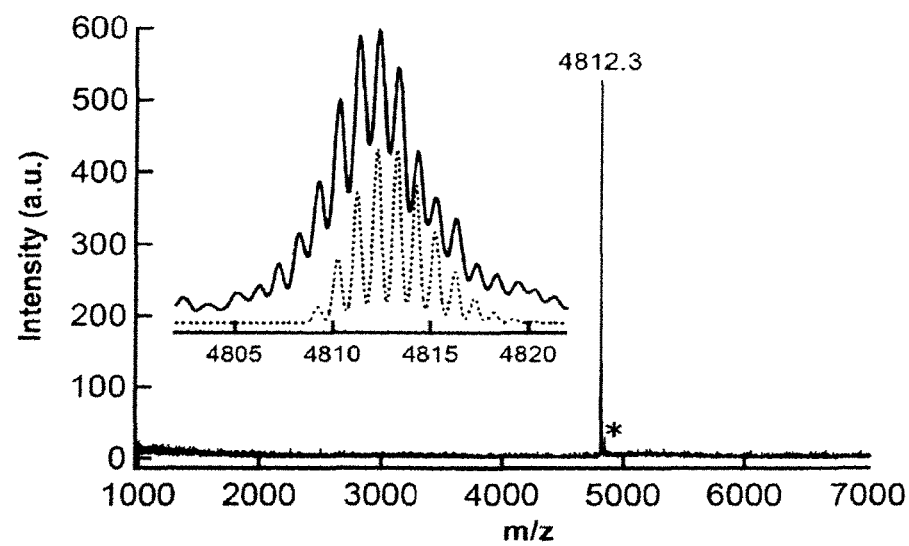
FIG. 11 shows an isotope-resolved MALDI-TOF mass spectroscopy (MS) mass spectrum of the quantum dot of FIG. 7.
Figure 12:
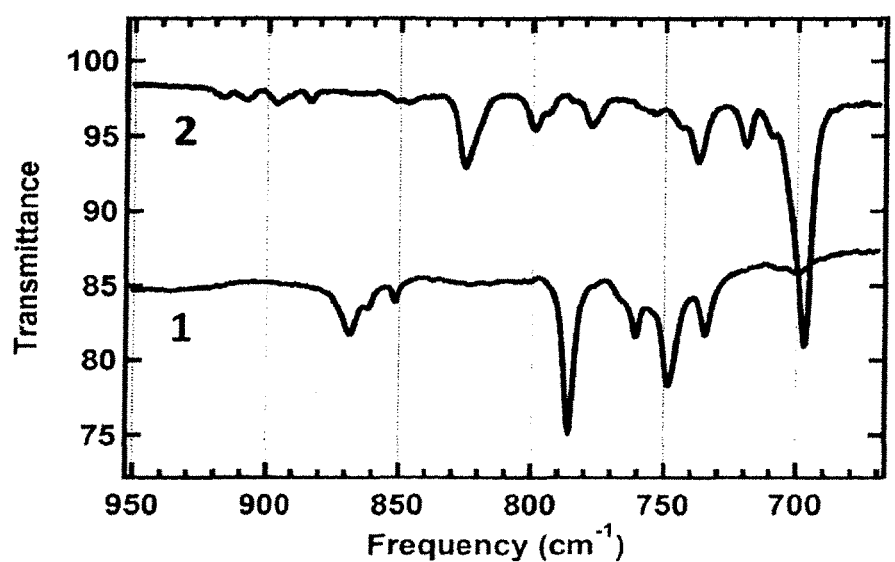
FIG. 12 shows the infrared (IR) absorption spectrum in the range corresponding to aromatic C—H out-of-plane bending modes for the quantum dot of FIG. 7 (curve 1)
Figure 13:
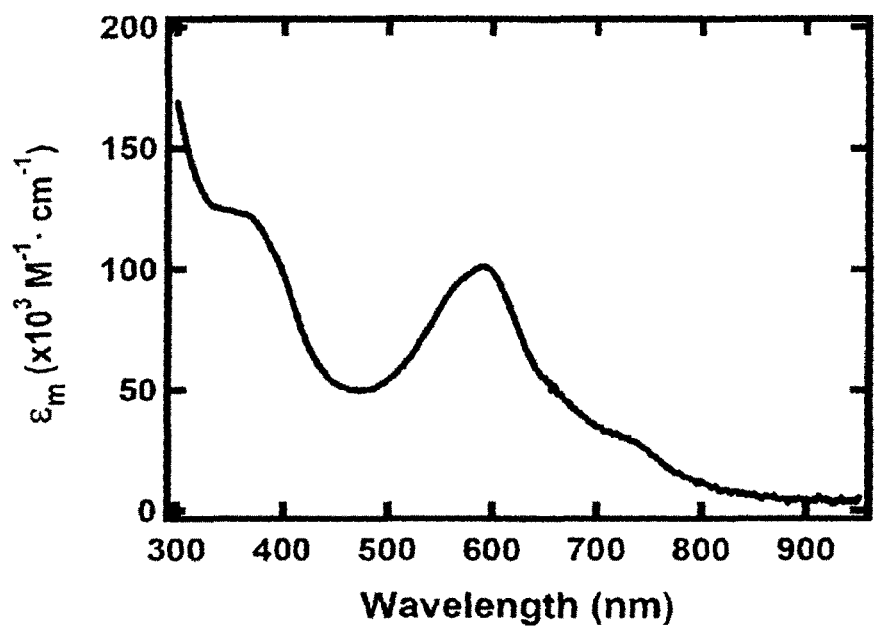
FIG. 13 shows the optical absorption spectrum (molar extinction coefficient $\varepsilon_m$) of the quantum dot of FIG. 7 in dichloromethane.
Figure 14:
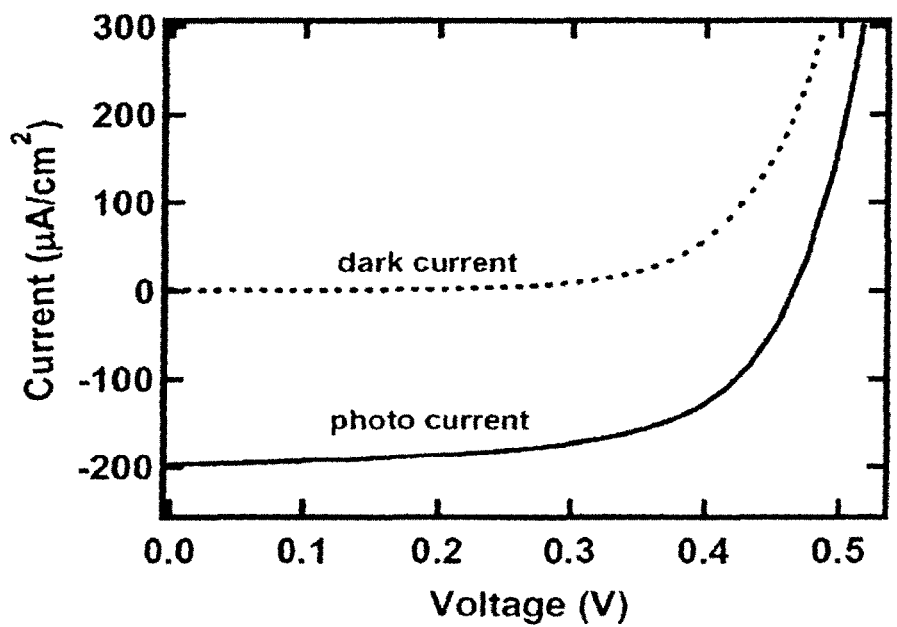
FIG. 14 shows the current-voltage characteristics of a typical nanocrystalline $TiO_2$ solar cell sensitized by the quantum dot of FIG. 7, in the dark and under illumination, respectively.
Figure 15:
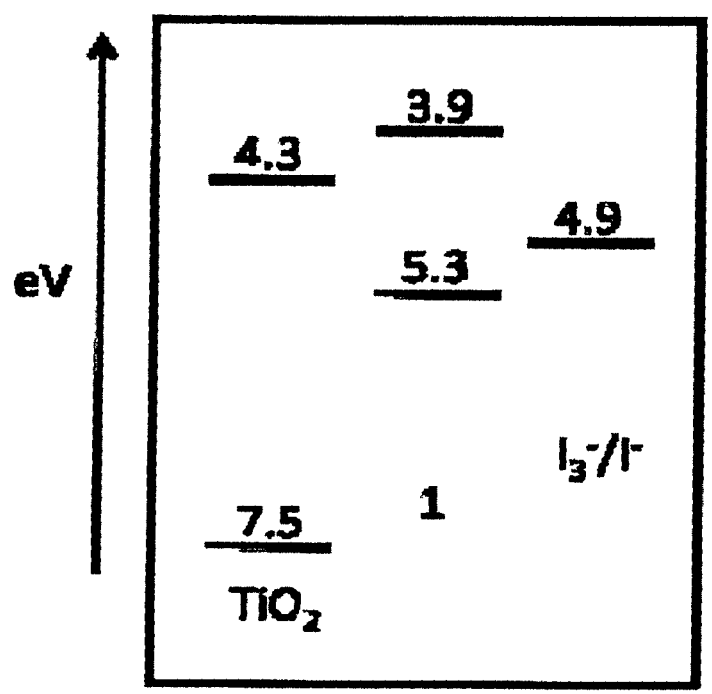
FIG. 15 shows the HOMO and LUMO energy levels of the quantum dot of FIG. 7, band levels of $TiO_2$, and reduction potential of $I_3^-/I^-$ (all values are below the vacuum level in electron volts)
Figure 16:
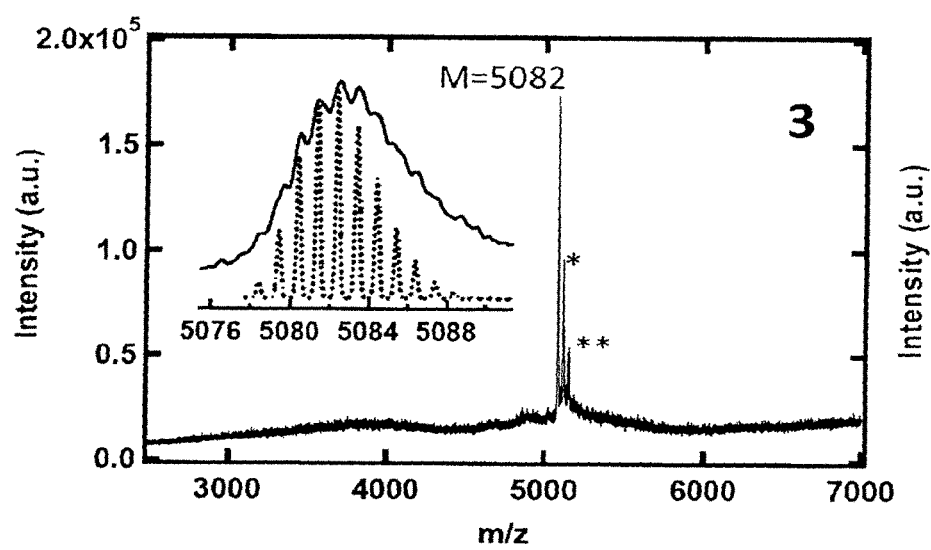
FIG. 16-19 show the MALDI-TOF MS spectra of quantum dots products made according to the described methods.
Figure 17:
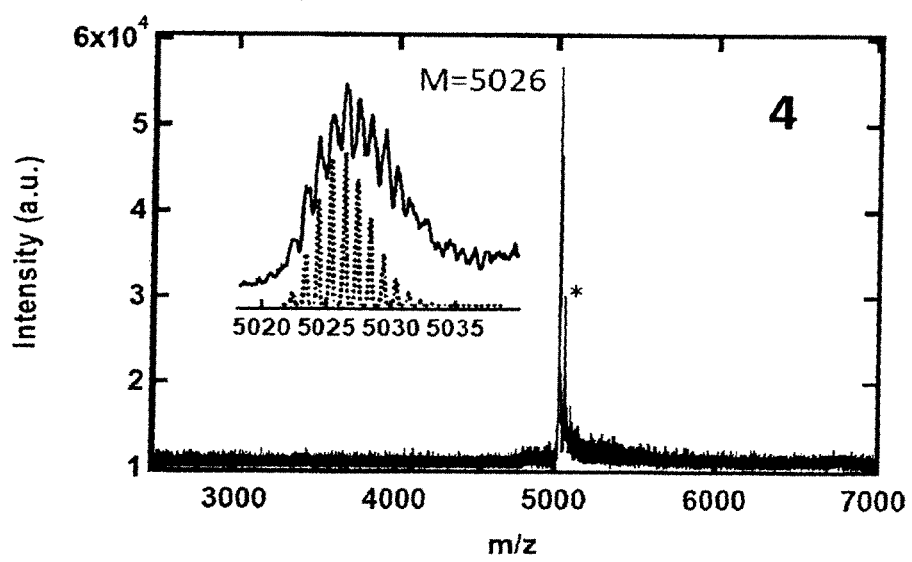
Figure 18:
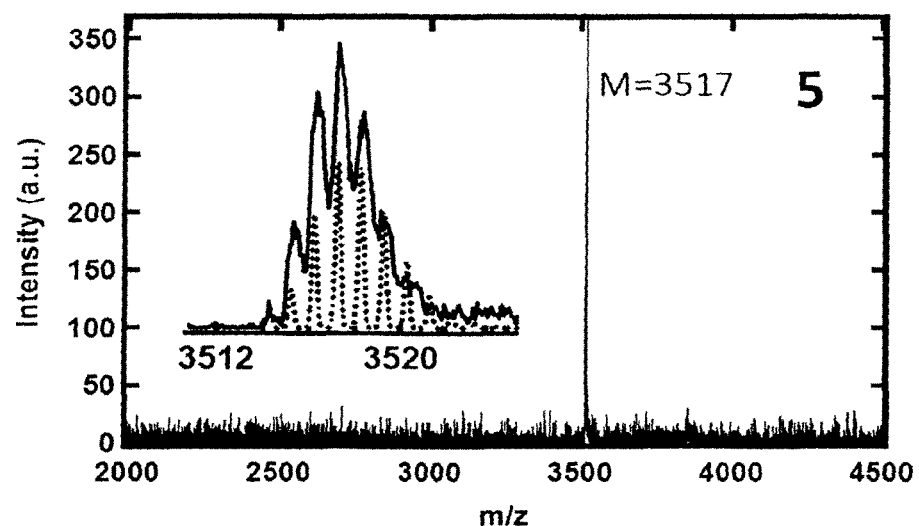
Figure 19:
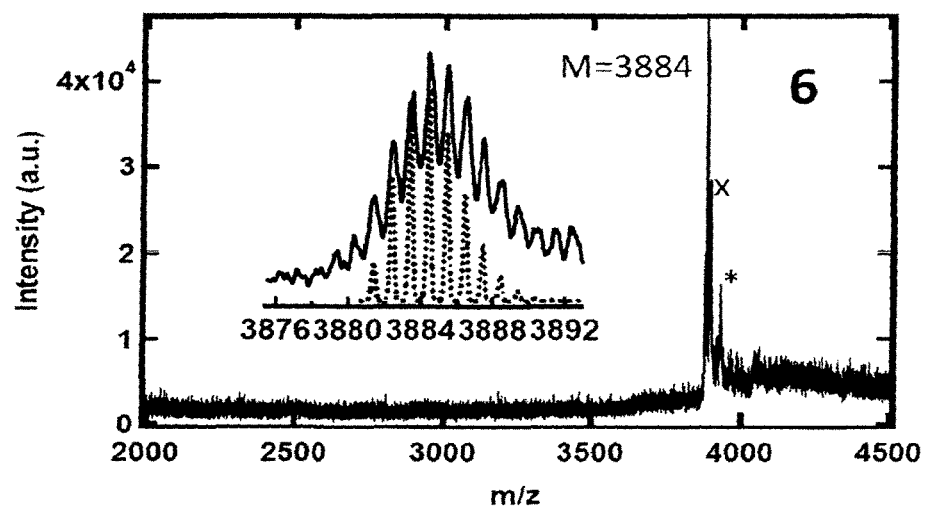

So that the nature of the products may be more fully understood, FIG. 11-15 show various analytical data obtained by analyzing the quantum dot shown in FIG. 7. FIG. 11 shows an isotope-resolved MALDI-TOF mass spectroscopy (MS) mass spectrum of the quantum dot of FIG. 7. FIG. 12 shows the infrared (IR) absorption spectrum in the range corresponding to aromatic C—H out-of-plane bending modes for the quantum dot of FIG. 7. FIG. 13 shows the Absorption spectrum (molar extinction coefficient $\varepsilon_m$) of the quantum dot of FIG. 7 in dichloromethane. In illustrative embodiments, the composition has an absorption spectrum having an absorption peak from about 350 nm to about 3000 nm associated with a HOMO to LUMO electronic transition. In one embodiment, the composition has an absorption spectrum having an absorption peak between about 450 nm to about 1500 nm associated with a HOMO to LUMO electronic transition. In another embodiment, the composition has an absorption spectrum having an absorption peak between about 450 nm to about 1000 nm associated with a HOMO to LUMO electronic transition. FIG. 14 shows the current-voltage characteristics of a typical nanocrystalline $TiO_2$ solar cell sensitized by the quantum dot of FIG. 7, in the dark and under illumination, respectively. FIG. 15 shows the HOMO and LUMO energy levels of the quantum dot of FIG. 7, band levels of $TiO_2$, and reduction potential of $I_3^-/I^-$ (all values are below the vacuum level in electron volts).

Another aspect of the present disclosure is that the versatility of carbon chemistry allows for tuning of graphenes to improve their performance in solar energy conversion. Described herein is the covalent functionalization of colloidal graphene quantum dots to improve their affinity to inorganic surfaces such as nanocrystalline $TiO_2$ surfaces. This can be directly applied to dye-sensitized solar cells and photo-induced charge injection. As a result, the energy conversion efficiency of the devices can be significantly enhanced.

Dye sensitization of nanocrystalline semiconductors is useful for converting solar radiation to low-cost electricity or fuels. In this approach, materials harvesting light and transporting charge carriers are separate, making it possible to select from varieties of materials with desired properties with great flexibility as the active components in the devices. The light harvesting materials can be selected to have desired absorption spectra as well as proper redox potentials to go with the charge transporting materials for light-induced charge injection. To optimize the light-induced charge injection, various linkers or functional groups can be applied, to improve the interfaces between the light harvesting materials with the charge transporting media and to enhance their electronic coupling.

One aspect of the present disclosure is that colloidal graphene quantum dots (QDs) can be functionalized to improve their ability to interface with semiconducting metal oxides. It is shown that covalently attaching a coupling groups (e.g. carboxylic acid groups) significantly improves the performance of the photovoltaic devices. Without being bound by theory, it is believed that the acids not only increase the binding affinity of the QDs to the metal oxides but also facilitate charge injection. Covalently adding the carboxylic acid groups also varies the redox potentials of the QDs, allowing for independent tuning their bandgaps and redox potentials to improve the performance of photovoltaics. Another aspect of the present disclosure is that graphene quantum dots are very attractive in this application because they have remarkable electro-optical properties and that the versatility of carbon chemistry enables us to fine tune their properties for solar energy conversion. Here, disclosed is that functionalizing the quantum dots, provides a means for independently tuning their bandgaps and redox potentials, two key parameters as light harvesting media. The former is achieved by varying the size of the quantum dots, and the latter by covalently attaching electron-withdrawing or donating functionalities. This has led to significant improvement of the solar cell performance.

By controlling the orientation of nanostructures with anisotropic shapes it is possible to take advantage of their anisotropic electrical, optical, and transport properties in electro-optical devices. For large-area alignment of nanocrystals, so far orientations are mostly induced and controlled by external physical parameters, such as applied fields or changes in concentration. Another aspect of the present disclosure is that the assemblies of colloidal graphene quantum dots include a new type of disk-shaped nanostructures, on polar surfaces and the control of their orientations. The orientations of the graphene quantum dots can be determined, either in- or out-of-plane with the substrate, by chemical functionalization that introduces orientation-dependent interactions between the quantum dots and the surfaces.

To take advantage of their anisotropic properties for various electro-optical devices, controlled orientation of the nanocrystals over large areas has been intensively investigated. For example, starting from pre-formed nanorods, wires, or tubes, methods including spontaneous lyotropic liquid crystal formation, electric fields, shear flow, and solvent-evaporation-induced alignment, have been reported. In these methods, the orientations of the nanocrystals are controlled by the external physical conditions, of which the spatial and temporal characteristics determine the areas, rates, as well as the order parameters of the alignment. As an alternative approach to multi-length scale architectures, self-assembly directed by built-in molecular information in the structural components has been demonstrated in many molecular systems through various non-covalent interactions. To implement this approach to control the orientations of nanocrystals over large areas, however, has been quite challenging because of the difficulties in programming orientation-dependent interactions between them.

Graphene quantum dots (QDs) have properties resembling more nanocrystalline solids than molecules. For example, the graphene QDs have continuous absorption spectra in the UV-visible region, due to the overlap of electronic absorption bands caused by closely spaced electronic energy levels and vibronic coupling. Graphene QDs have very slow hot-carrier cooling dynamics, reminiscent of "phonon bottleneck" intensively investigated in conventional semiconductor quantum dots. Because the graphene QDs can be processed from solution and have size- and shape-dependent optical properties, they may be used as light absorbers for thin-film solar cells. By making them with sizes around 2.5 nm, QDs can have an absorption edge up to 900 nm (~1.4 eV), the optimal value for single-junction solar cells under non-concentrated sunlight. In comparison with other light absorbers such as ruthenium complexes and inorganic quantum dots that absorb light in the whole visible range, the graphene QDs are primarily made of abundant elements on earth and don't contain rare or toxic heavy metals. In addition, the stepwise solution chemistry approach to the graphene QDs allows for precise control of their structures and functionalization.

Described herein is orientation control of graphene QDs on polar surfaces through chemical functionalization. Langmuir techniques and atomic force microscopy (AFM) are used to illustrate the design principles to control the assemblies of the QDs on water and mica surfaces; water and mica surfaces are shown because the serve as model systems for polar semiconducting oxide surfaces used in dye-sensitized solar cells.

In another embodiment, the composition has a solubility maximum in a non-polar solvent of from about 10 mg/mL to about 100 mg/mL. In yet another embodiment, the composition has a solubility maximum in a non-polar solvent of from about 20 mg/mL to about 70 mg/mL. In one embodiment, the composition has a solubility maximum in a non-polar solvent of from about 25 mg/mL to about 50 mg/mL. While the nature and identity of the organic solvent has an effect on the solubility, the ranges used here describe the solubility in exemplary non-polar solvent such as chloroform, toluene, or tetrahydrofuran. In illustrative embodiments, a method of preparing a large soluble graphene comprising attaching a hindering group to one or more edges of the graphene is disclosed. In one embodiment, the method comprises attaching substituted phenyl moieties to the edges of the graphene. In another embodiment, the phenyl. moieties are substituted with one or more alkyl groups. In another embodiment, the phenyl moieties are trialkyl substituted. In another embodiment, the trialkyl substituted phenyl moieties are alkylated at the 1, 3, and 5 carbon positions. In another embodiment, the substituted phenyl moieties comprise a substituent attached to at least one carbon position ortho- to the graphene. In another embodiment, the soluble graphene comprises at least 100 conjugated carbon atoms. In another embodiment, the soluble graphene comprises at least 150 conjugated carbon atoms. In another embodiment, the soluble graphene comprises at least 168 conjugated carbon atoms.

In illustrative embodiments, a black dye comprising a large soluble graphene is disclosed. In further illustrative embodiments, a photovoltaic device comprising a large graphene quantum dot is disclosed. In another illustrative embodiment, a solar cell comprising a sensitizer comprising large graphene quantum dots is disclosed. As used herein, "room temperature" refers to from about 20° C. to about 25° C. As used herein, "soluble graphene" refers to a graphene that does not aggregate in solution and is soluble at concentrations in excess of that concentration which would be considered "sparingly soluble." For example, a graphene that exhibited a maximum solubility of 0.01 mg/ml would be considered a soluble graphene. However, the soluble graphenes described herein are soluble at much higher concentrations; for example, up to but not limited to 30 mg/ml at room temperature in an organic solvent, including but not limited to, for example, chloroform, tetrahydrofuran, or toluene.

As used herein, "hindering group" refers to a chemical group attached to a graphene which is able to reduce the effect of inter-graphene attractive forces in solution sufficiently to reduce or prevent graphene aggregation, particularly face-to-face graphene stacking. A hindering group may exert its effects alone or in combination with other hindering groups. As used herein, "large graphene" refers to a graphene that contains at least 100 conjugated carbon atoms, and more particularly over 150 conjugated carbon atoms.

To reduce the tendency of forming insoluble aggregates by large graphene nanostructures, the graphenes are shielded from one another by enclosing them in all three dimensions. This can be achieved by covalently attaching hindering groups. Preferably, the hindering groups are sufficiently bulky such that they prevent face-to-face stacking of the graphene via steric hindrance. The hindering groups may comprise substituted phenyl moieties that are di-, tri-, tetra-, penta-, or hexa-substituted. For example, 1,3,5-trialkyl-substituted phenyl moieties are attached (at the 2-position) to the edges of the graphenes (FIG. 7). Without being bound by theory, it is believed that the crowdedness on the edges forces the peripheral phenyl groups to twist from the plane of the graphene, resulting in the alkyl chains at 1,3-positions extending out of the plane and the one at 5-position extending laterally. This leads to increased distance between graphenes in all three dimensions, and thus greatly reduces the inter-graphene attraction due to its short range.

EXAMPLES

The following graphene molecular structures were prepared:

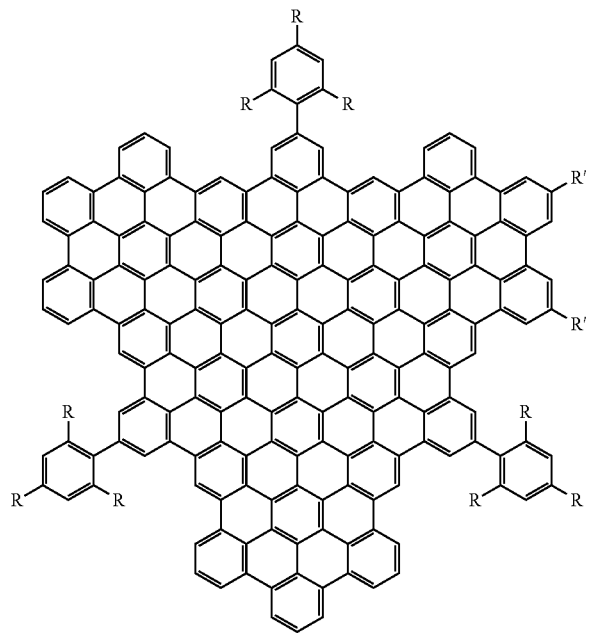

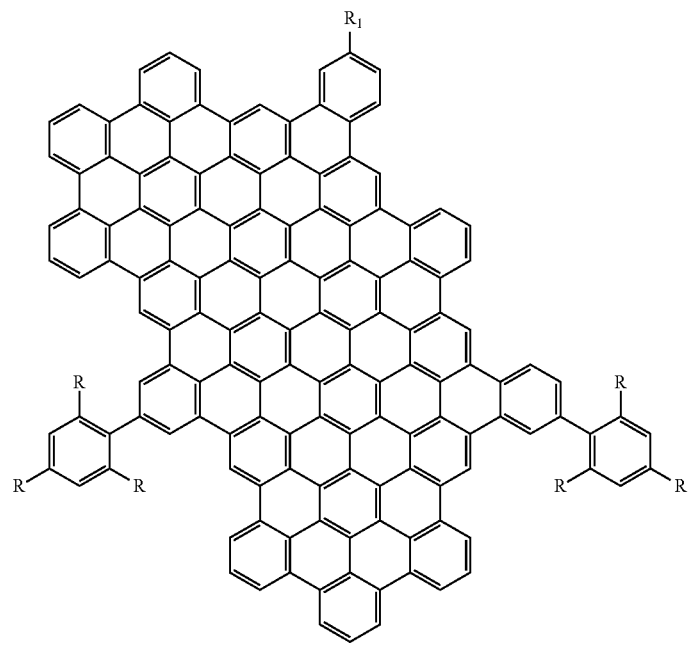

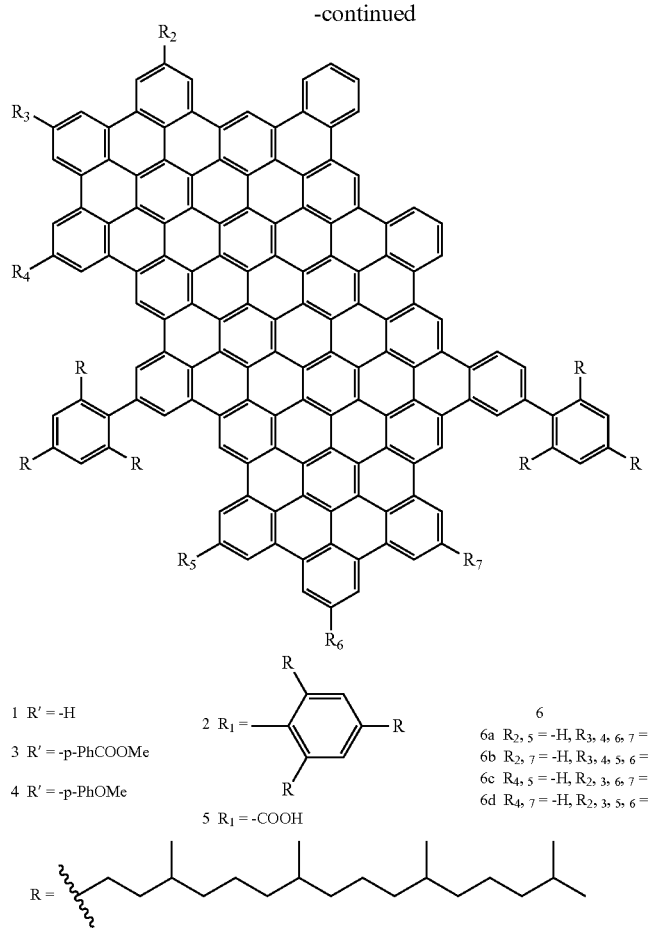
1 R' = -H
2 R₁ = (substituted phenyl)
3 R' = -p-PhCOOMe
4 R' = -p-PhOMe
5 R₁ = -COOH
6
6a R₂,₅ = -H, R₃,₄,₆,₇ = -PhOMe
6b R₂,₇ = -H, R₃,₄,₅,₆ = -PhOMe
6c R₄,₅ = -H, R₂,₃,₆,₇ = -PhOMe
6d R₄,₇ = -H, R₂,₃,₅,₆ = -PhOMe
R = (phytyl chain)
Quantum dots (QDs) 1-6 were made according to the methods show in the following synthetic routes:
For the synthesis of graphene QDs 1 and 2:
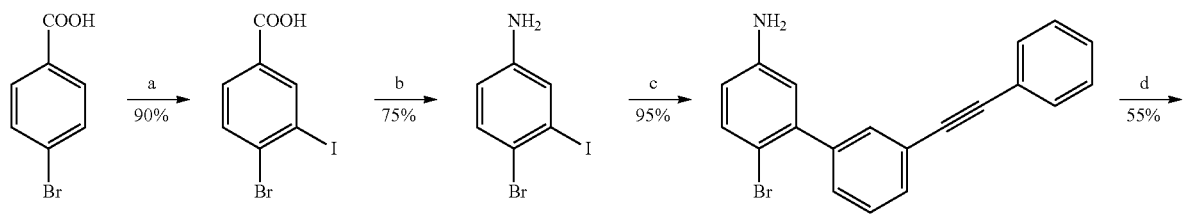
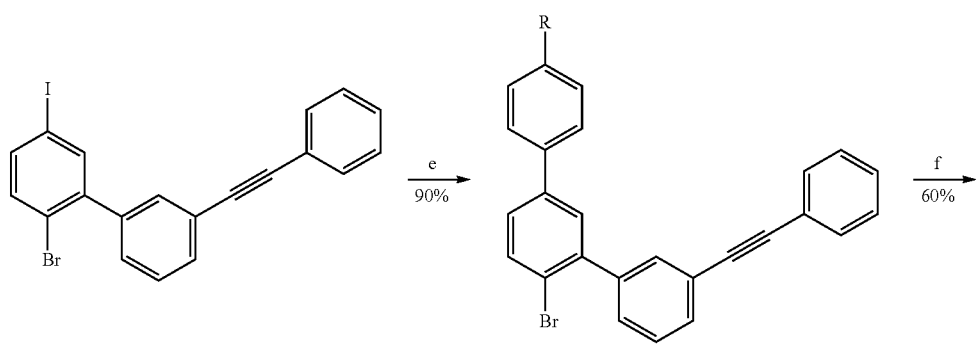

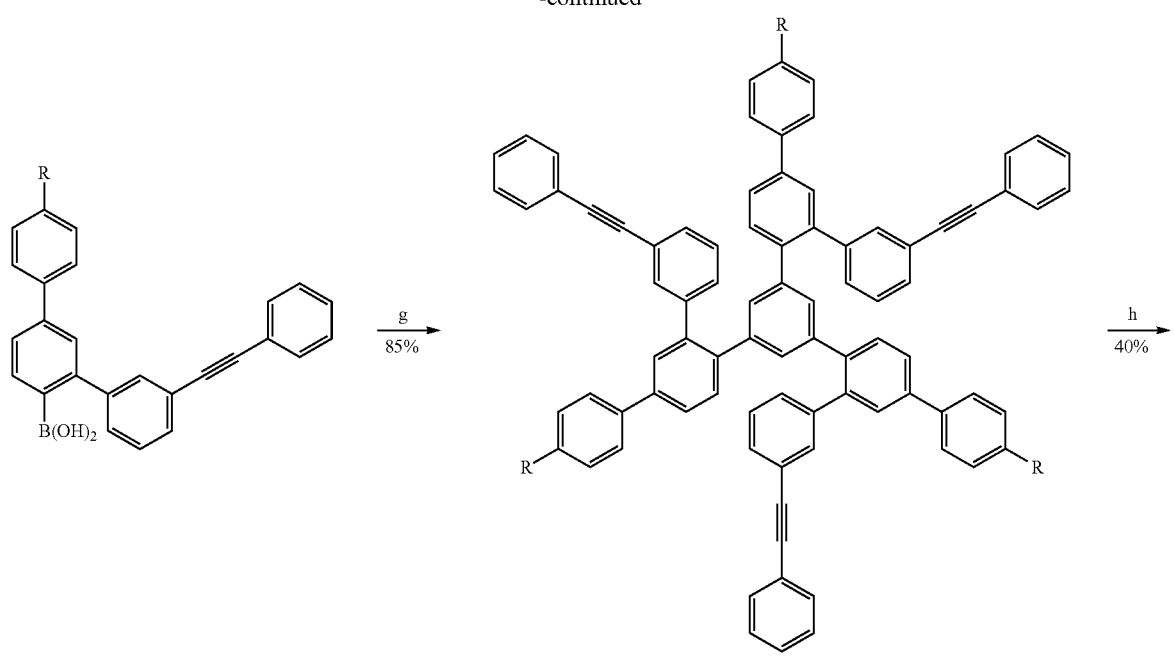
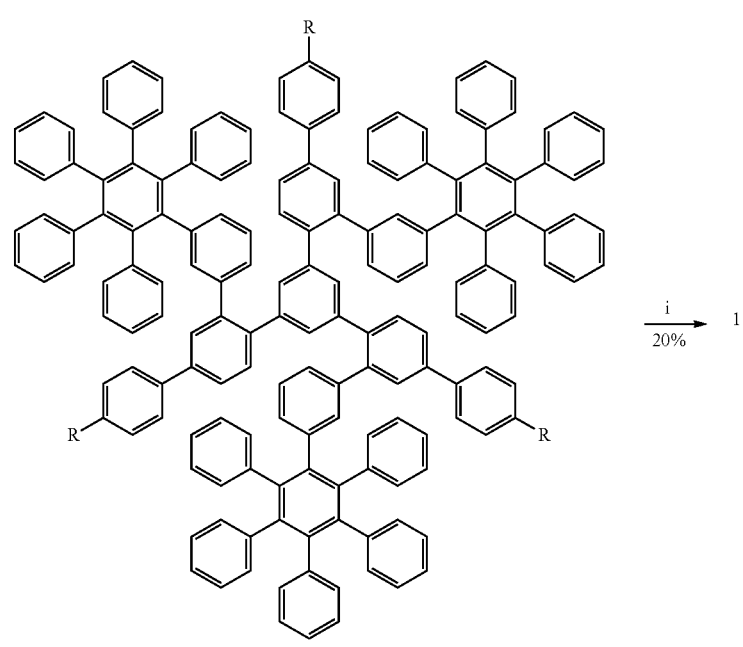

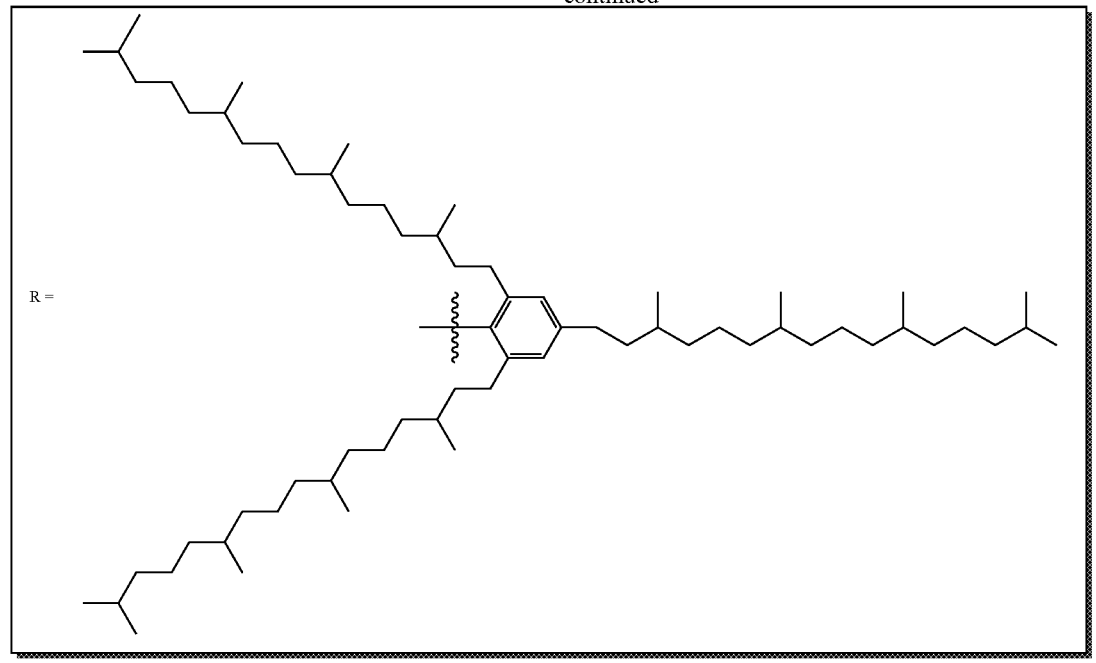

Steps: a: NaIO$_4$, I$_2$, concentrated H$_2$SO$_4$, room temperature. b: Heated with diphenylphosphoryl azide in triethylamine and tert-butanol at 80° C., followed by treatment with CF$_3$COOH in dichloromethane at room temperature. c: Suzuki condition with 3-(phenylethynyl)phenylboronic acid, Pd(PPh$_3$)$_4$, K$_2$CO$_3$ in water, ethanol, and toluene mixture, 60° C. d: Iodine and tert-butyl nitrite in benzene, 5° C. to room temperature. e: Suzuki condition with substituted phenyl boronic acid, Pd(PPh$_3$)$_4$, K$_2$CO$_3$ in water, ethanol, and toluene mixture, 80° C. f: Treatment with butyllithium in tetrahydrofuran (THF) at −78° C., then with triisopropyl borate at −78° C., followed by treatment with acidic water at room temperature. g: Suzuki condition with 1,3,5-triiodobenzene, Pd(PPh$_3$)$_4$, K$_2$CO$_3$ in water and toluene mixture, 80° C. h: Tetraphenylcyclopentadienone in diphenylether, 260° C. i: FeCl$_3$ in nitromethane and dichloromethane mixture, room temperature.

With the solubilization method described herein, starting from small organic compounds highly soluble graphene quantum dots (e.g. QD 1, FIG. 7) have been synthesized that contain 168 conjugated carbon atoms, believed to be the largest soluble QD reported so far. A colorless polyphenylene dendrimer 2, a precursor for 1, was first synthesized through stepwise reactions in solution according to the procedures outlined in above. Compound 2 has specially designed features to facilitate the yield of 1 in the subsequent oxidative condensation reaction. More specifically, the connectivity of the phenyl groups was chosen as such to avoid their rearrangement in the oxidative environments. In addition, to prevent aggregation of 1 when it is generated, 2 has the solubilizing trialkyl phenyl groups preinstalled. Subsequent treatment of compound 2 with FeCl$_3$ in chloroform/nitromethane mixture under a continuous flow of argon leads to a deep blue solution. Quenching of the reaction after 2 hours with methanol led to a black precipitate, which was then centrifuged for removal of the liquid, followed by repetitive dissolution in chloroform, precipitation with methanol, centrifugation, and decantation.

QD 1 was isolated from the black precipitate with reverse-phase high-performance liquid chromatography (HPLC), and its structural identification was supported by high-resolution MALDI-TOF mass spectroscopy and infrared (IR) vibrational spectroscopy. With commercial HPLC columns packed with octadecylsilane-functionalized silica and a tetrahydrofuran/dichloromethane mixture (50/50, v/v) as eluent, the major eluted fraction was collected and characterized. FIG. 11 shows its mass spectrum, with an isotope pattern consistent with that calculated for structure 1. FIG. 12 shows the IR absorption spectrum in the range corresponding to aromatic C—H out-of-plane bending modes, of which the resonance energy is known to be characteristic of the substitution pattern on phenyl rings. Referring again to FIG. 11, characterization of graphene QD 1 reveals a MALDI-TOF mass spectrum with a predominant peak at the mass of 1 (M=4812.3). (Inset) The isotope-resolved spectrum (solid line) with a calculated one for 1 (dotted line). FIG. 12 shows an IR absorption of C—H out-of-plane bending modes in 1 (bottom trace) and its precursor 2 (top trace). The transitions near 850 cm$^{-1}$ are due to isolated C—H bonds and those between 730 and 790 cm$^{-1}$ to adjacent ones. The weak peaks for 1 near 700 cm$^{-1}$ are due to out-of-plane skeletal vibrations. Referring back to FIG. 11, a small peak (marked by asterisk) is present corresponding to a mono-chlorinated product (M+34). Its quantity however is likely to have been over-emphasized in mass spectrum since no significant signal for C—Cl stretching is observed in FIG. 12. The presence of seven discernable transitions is consistent with the high symmetry of 1, which according to a symmetry analysis should have no more than eight in this range. The simple absorption pattern meanwhile indicates the high purity of the quantum dots obtained. Following the resonance energy for substituted phenyl groups, the three transitions near 850 cm$^{-1}$ can be assigned to the bending of the isolated C—H bonds on the tetra- or penta-substituted phenyl rings. The four lower-energy transitions between 730 and 790 cm$^{-1}$ can be assigned to those adjacent ones on tri-substituted phenyl rings. Using conventional liquid phase NMR spectroscopy, the aromatic proton resonance peaks were not detected.

Graphene QD 1 is highly soluble in various common organic solvents, such as chloroform, tetrahydrofuran, toluene, and the like, with solubility up to 30 mg/ml at room temperature. Without being bound by theory, the large solubility may be rationalized by an energy-minimized geometry obtained with force field calculation. Three pairs of alkyl chains enclose the aromatic core from both sides of the graphene plane, effectively preventing the graphene moieties from approaching each other and thus preventing their aggregation. The solubilization method illustrated herein with a graphene containing 168 conjugated carbons is also applicable for preparing soluble graphenes with fewer or more than 168 conjugated carbon atoms.

The large solubility of the well-defined graphene quantum dots makes them a useful class of materials to interface with other active components for complex functions. For example, their wide light absorption spectrum and large molar extinction coefficients, together with their ready availability, make the quantum dots useful for photovoltaic applications. Illustratively, photovoltaic devices have been fabricated with 1 as a sensitizer. Due to its large size, quantum dot 1 absorbs a wide spectrum of light from visible to near infrared (IR). FIG. 13 shows their molar extinction coefficients ($\varepsilon_m$) in dichloromethane in the visible-near IR region. An absorbance maximum appears at 591 nm, with $\varepsilon_m = 1.0 \times 10^5$ $M^{-1}$ $cm^{-1}$. FIG. 15 shows the HOMO and LUMO energy levels of 1, band levels of $TiO_2$, and reduction potential of $I_3^-/I^-$. FIG. 14 shows the current-voltage characteristics of a typical nanocrystalline $TiO_2$ solar cell sensitized by 1, in the dark and under illumination, respectively.

The absorption edge extends up to 900 nm, the optimal energy threshold that enables the thermodynamic limit of energy conversion efficiency in single-junction solar cells under non-concentrated sunlight. With cyclic voltammetry and the absorption spectrum, the energy levels of the highest occupied and the lowest unoccupied molecular orbitals (HOMO and LUMO) of 1 were determined to be at 5.3 and 3.9 eV below the vacuum level, respectively. These values, relative to band levels of $TiO_2$ and reduction potential of $I_3^-/I^-$ (FIG. 15), permit the use quantum dot 1 as a sensitizer in dye-sensitized solar cells made of nanocrystalline $TiO_2$ particles. Upon photo-excitation, in principle QD 1 is capable of injecting an electron to $TiO_2$ and then getting regenerated by accepting an electron from $I^-$.

The synthetic schemes for preparing QDs 3-6 are summarized in the following reaction schemes, which are based on the routes for 1 and 2 and functionalization of hexa-peri-hexabenzocoronene derivatives. For all the QDs, we started with synthesizing polyphenylene dendrimeric precursors (12, 13, 19, 27) and subsequently oxidized them to form the graphene moieties. All the precursor have the solubilizing 1,3,5-trialkyl-substituted phenyl groups preinstalled to prevent the graphene QDs from aggregating when they are made. The trialkyl-substituted phenyl groups twist from the plane of the graphene due to the crowdedness on the edges, resulting in the alkyl chains spanning a three-dimensional cage that prevents the graphene QDs from approaching each other.

For the synthesis of graphene QDs 3, 4 and 14[a]:

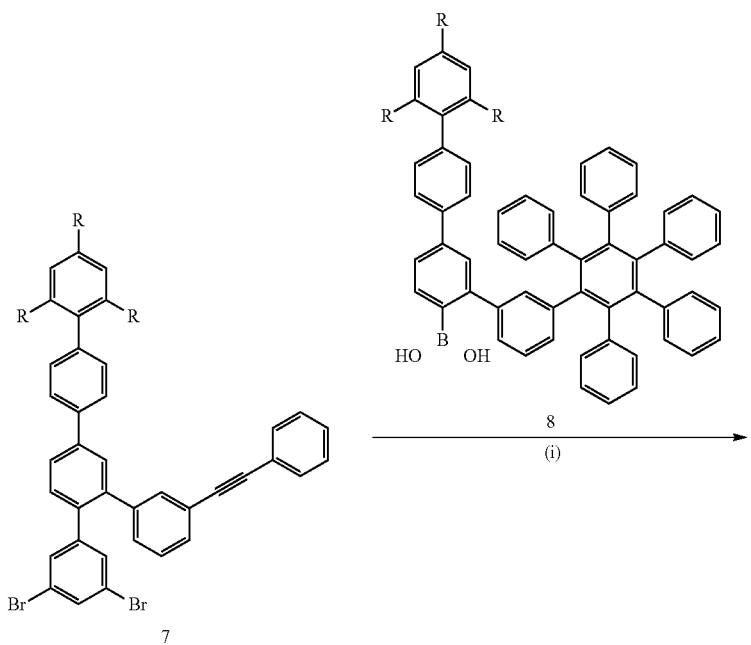

-continued
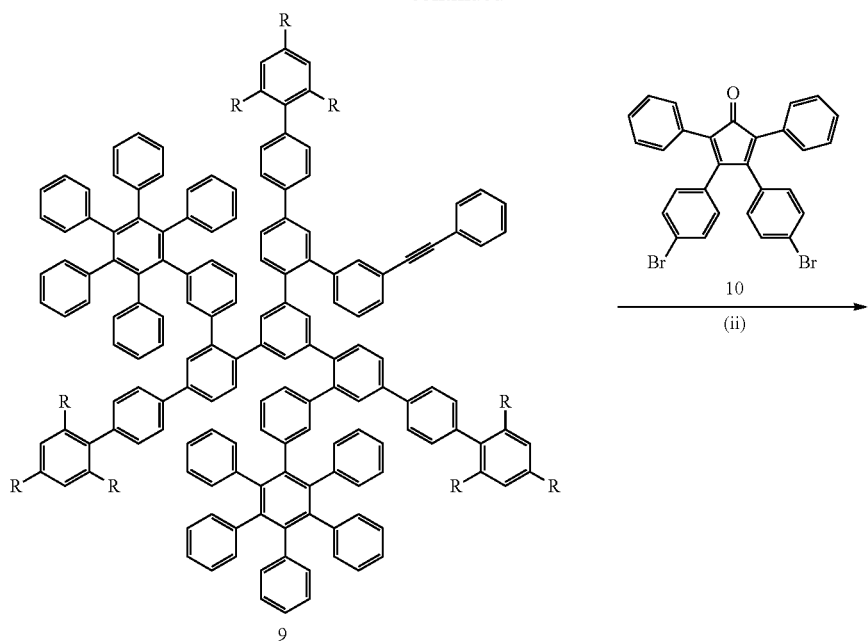
9
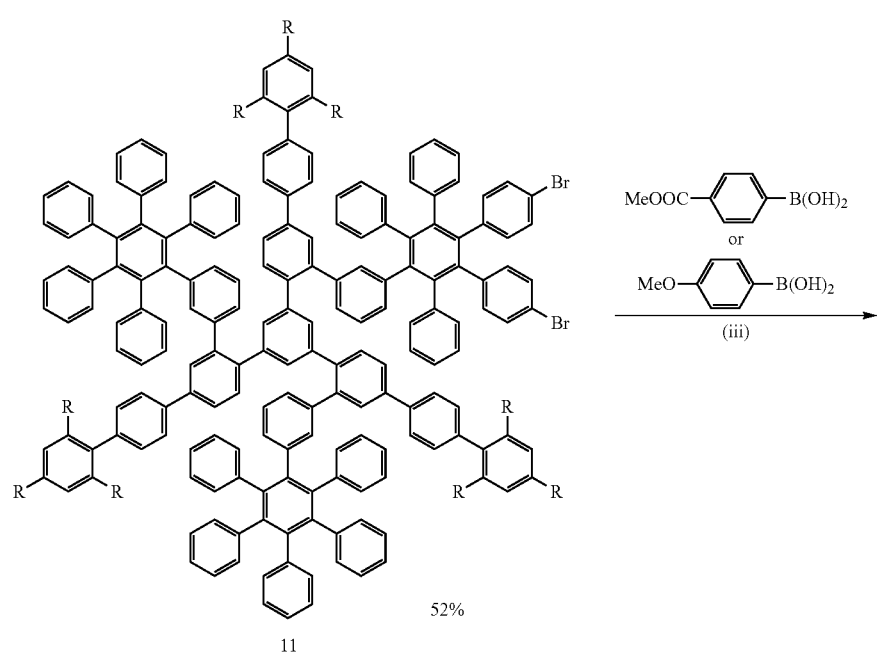
11 52%

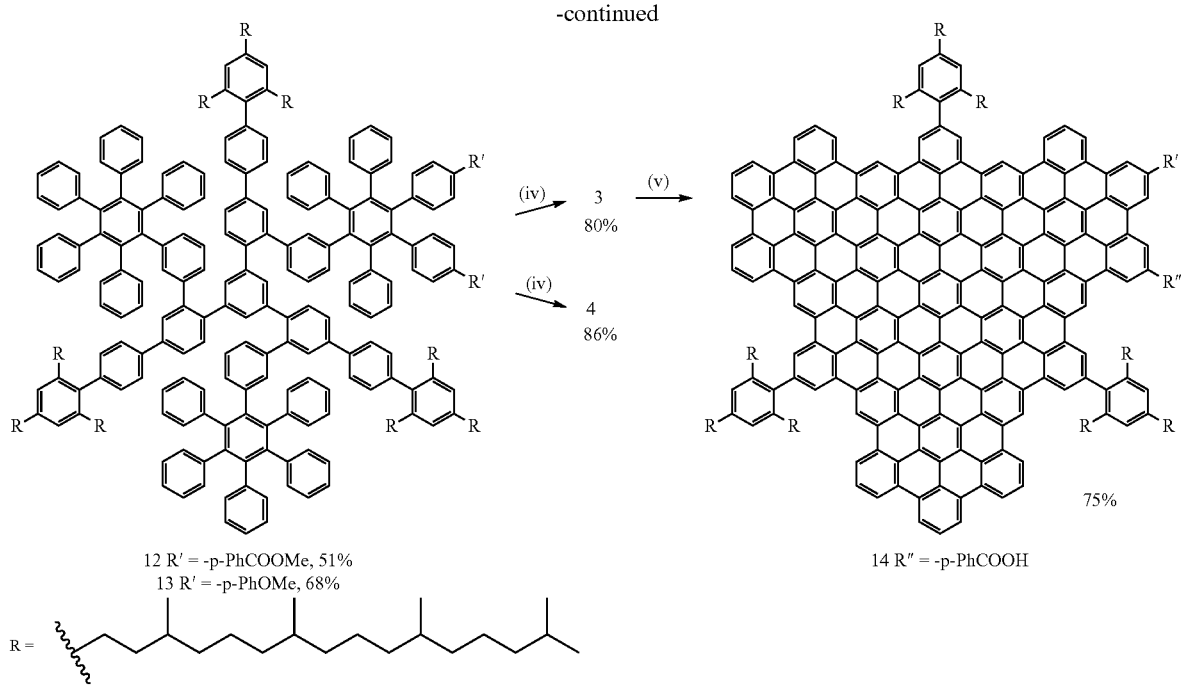

12 R' = -p-PhCOOMe, 51%
13 R' = -p-PhOMe, 68%

14 R" = -p-PhCOOH $^{a}$Conditions: (i) Pd(PPh$_3$)$_4$, K$_2$CO$_3$, toluene, EtOH, H$_2$O, 80° C.; (ii) diphenyl ether, reflux; (iii) Pd(PPh$_3$)$_4$, K$_2$CO$_3$, toluene, MeOH, H$_2$O, 80° C., 4-Methoxycarbonylphenylboronic acid for 12 and 4-Methoxyphenylboronic acid for 13; (iv) FeCl$_3$, CH$_2$Cl$_2$, CH$_3$NO$_2$; (v) BBr$_3$, CH$_2$Cl$_2$, 0° C.

Intermediates 7, 8, 15, and 24 were prepared following procedures developed to synthesize graphene QDs with low molecular symmetry. Repetitive of Suzuki coupling and the Diels-Alder reaction yielded polyphenylene dendrimeric precursors 12, 13, 19, and 27, which were then oxidized with FeCl$_3$ in a CH$_2$Cl$_2$/CH$_3$NO$_2$ mixture under a constant flow of nitrogen to produce the graphene QDs. Quenching of the reaction after 1-2 hours with methanol led to a black (3, 4) or deep red (20, 6) precipitate, which was then centrifuged for removal of the liquid, followed by repetitive dissolution in toluene, precipitation with methanol, centrifugation, and decantation. For the Diels-Alder reaction, 3,4-bis(4-bromophenyl)-2,5-diphenylcyclopenta-2,4-dienone (10) and 3,4-bis(4'-methoxy-[1;1'-biphenyl]-4-yl)-2,5-diphenylcyclopenta-2,4-dienone (26) were made with literature methods. All the QDs obtained are highly soluble in common organic solvent such as chloroform, toluene, THF, etc., demonstrating the effectiveness of our solubilization strategy.

For the synthesis of graphene quantum dot 5 and 6$^{a}$:

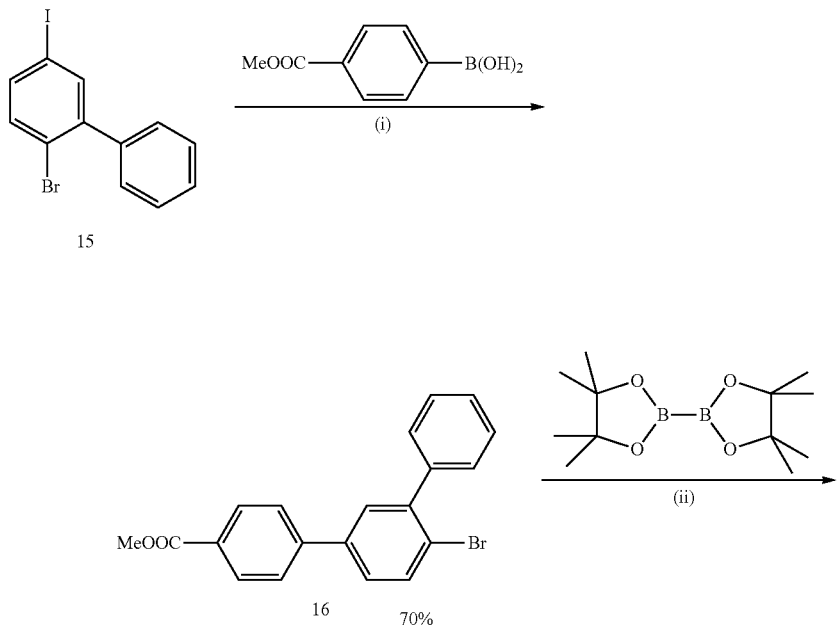

-continued
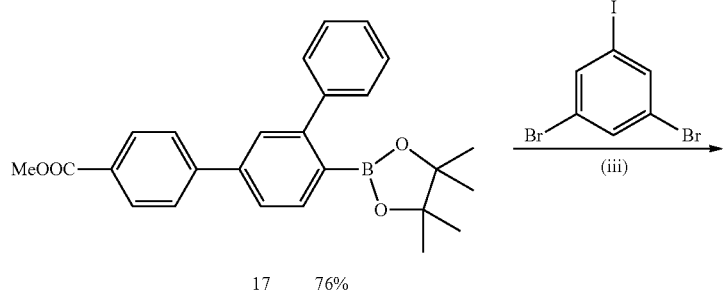
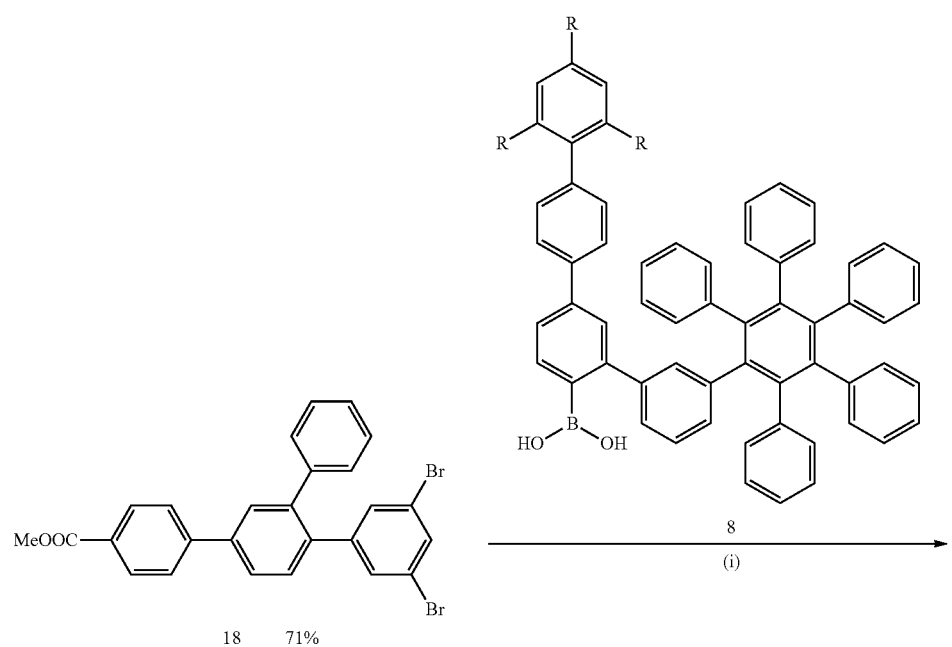
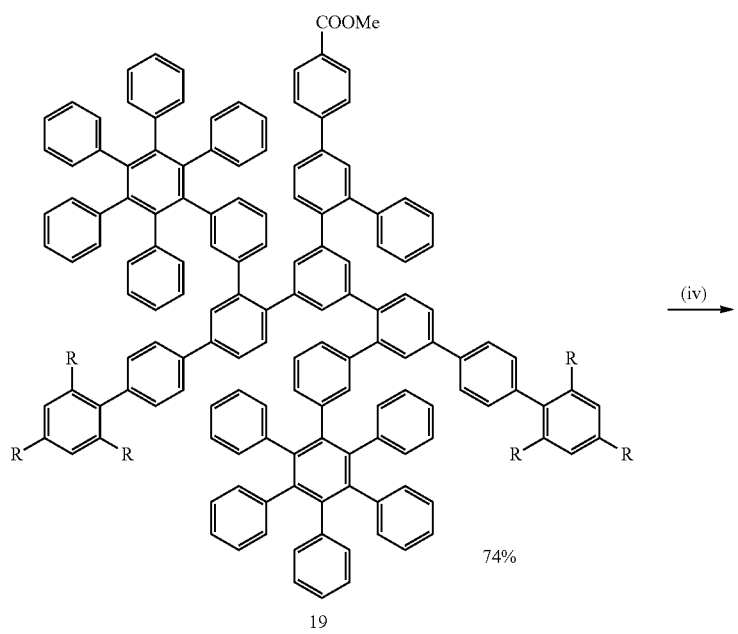

-continued
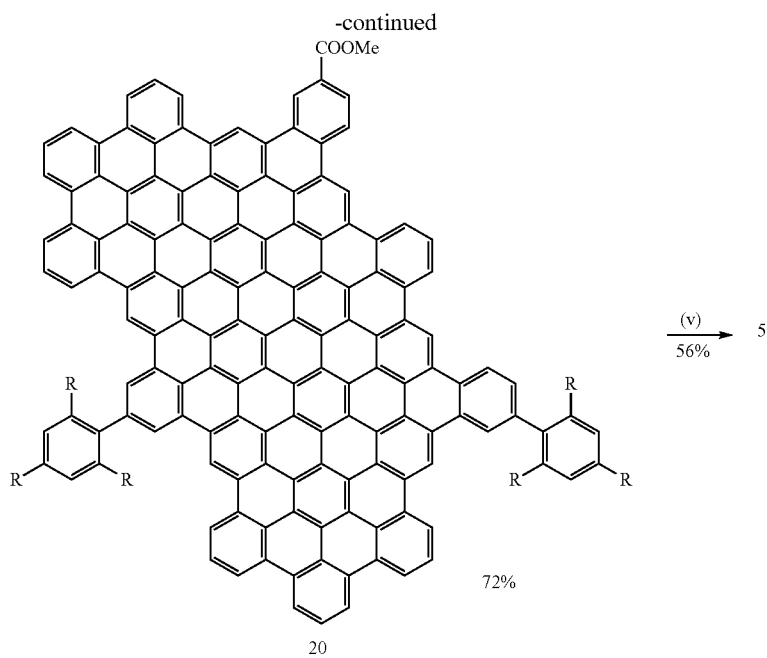
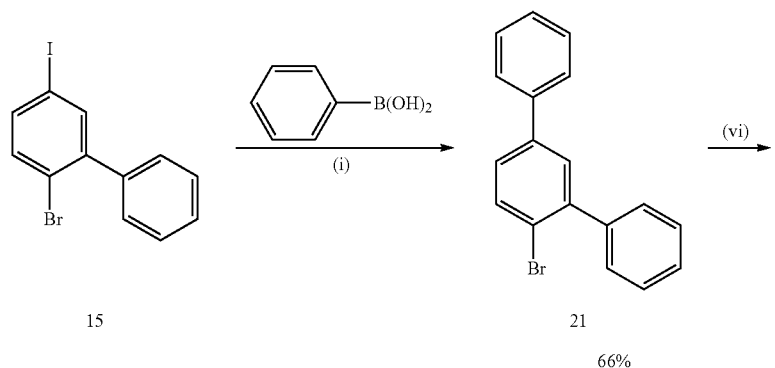
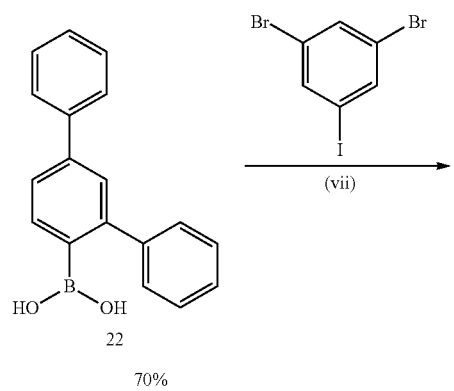

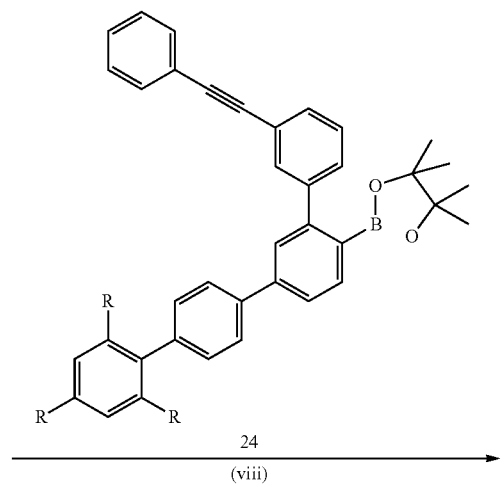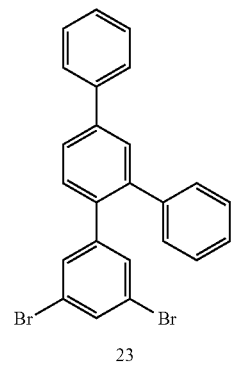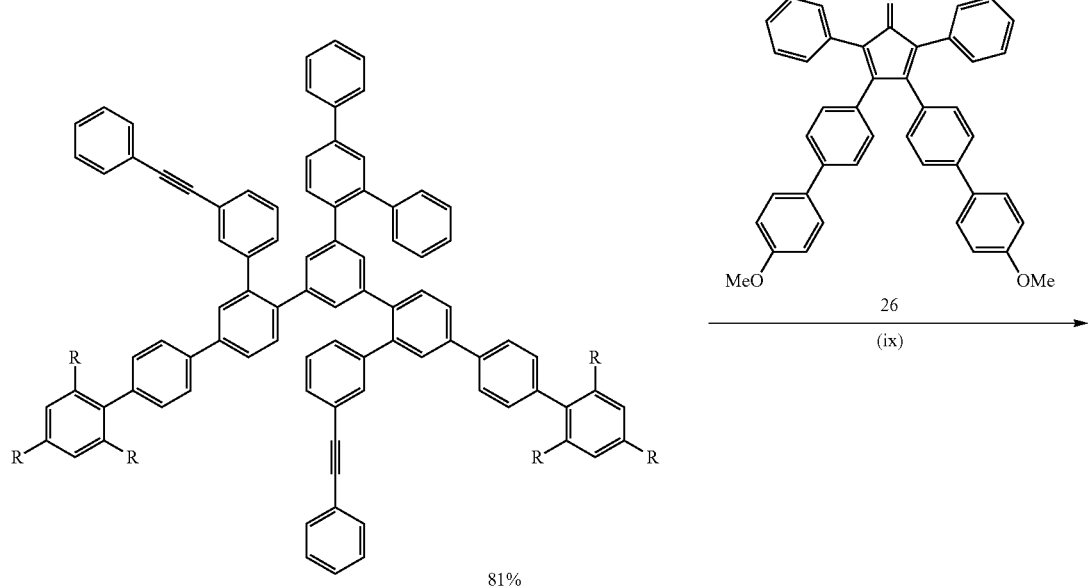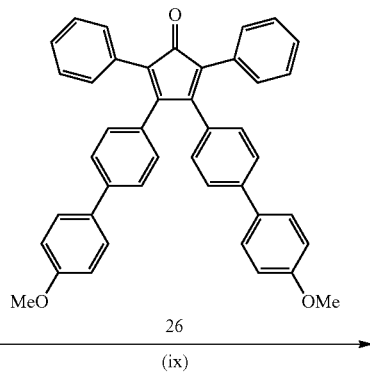

-continued

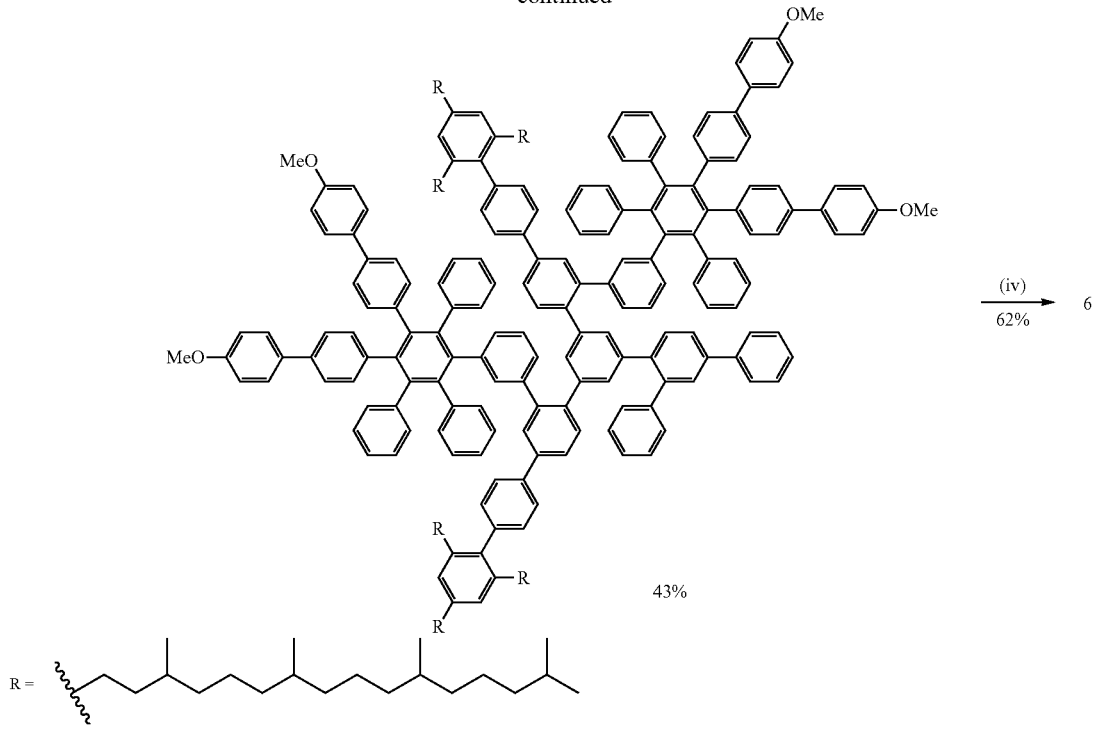

Conditions: (i) Pd(PPh$_3$)$_4$, K$_2$CO$_3$, toluene, MeOH, H$_2$O, 80° C.; (ii) Pd(OAc)$_2$, K$_3$PO$_4$, 2-dicyclohexylphosphino-2',6'-dimethoxybiphenyl, toluene, H$_2$O, 80° C. (iii) Pd(PPh$_3$)$_4$, K$_2$CO$_3$, toluene, MeOH, H$_2$O, 65° C.; (iv) FeCl$_3$, CH$_2$Cl$_2$, CH$_3$NO$_2$; (v) BBr$_3$, CH$_2$Cl$_2$, 0° C.; (vi) (a) n-BuLi, THF, -73° C.; (b) B(i-PrO)$_3$; (c) HCl, H$_2$O; (vii) Pd(PPh$_3$)$_4$, K$_2$CO$_3$, toluene, EtOH, H$_2$O, 65° C.; (viii) Pd(PPh$_3$)$_4$, K$_2$CO$_3$, toluene, EtOH, H$_2$O, 80° C., (ix) diphenyl ether, reflux.

While all the reaction intermediates to the graphene QDs were purified with silica gel chromatography and confirmed with standard characterization methods, due to dynamic aggregation of the graphene QDs in solution and fast spin-spin relaxation, the aromatic protons could not be detected with conventional liquid phase NMR spectroscopy, even at elevated temperatures. As a result, the graphene QDs were identified with isotope-resolved MALDI-TOF mass spectroscopy (MS) (FIG. 16-19), which has been the most effective applicable method for ensemble characterization of large graphene nanostructures. Referring now to FIG. 16-19, shown are the MALDI-TOF MS spectra of quantum dots 3-6. In the insets are the isotope-resolved patterns experimentally observed (solid curves) with ones calculated (dotted curves) from the molecular structures. In the spectra of 3, 4, and 6, the peaks marked by an asterisk are due to mono-chlorinated byproducts (M+34), and the one marked by two asterisks due to bi-chlorinated byproducts (M+68) in the last oxidation step. In the case of 6, the peak marked by an "x" corresponds to M+12, probably partially oxidized products. By comparing the experimental spectra with simulated ones, the targeted QDs to be the major components in the final products could be identified. Meanwhile the MS spectra also indicated the presence of a small amount of mono- or di-chlorinated products as well as partially oxidized ones. Either normal phase or reverse phase chromatography techniques were not able to remove the impurities from the QDs, and therefore the QDs were used for subsequent studies without further purification. However, as discussed below, it is possible to exclude the contribution of the impurities with spectroscopic techniques that selectively interrogate the QDs with desired structures. Further, in the case of 6, because of the multiple conformation of the precursor 27, the resultant oxidation product 6 is a mixture of four isomers (6a-d). No further attempts were made to separate them, since they are likely to have similar optical and electronic properties.

The carboxylated graphene QDs 3 and 20 were deprotected with BBr$_3$ in dichloromethane in the dark, yielding QDs 14 and 5 with free carboxylic acid groups. 14 and 5 were subsequently precipitated and washed with large volume of methanol, and used for subsequent studies.

Figure 20:
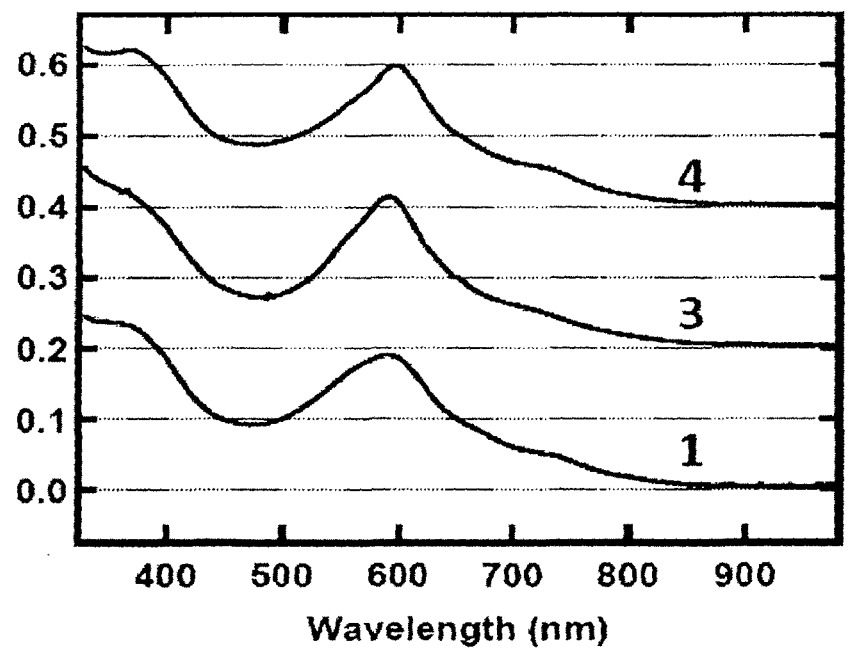
FIG. 20-21 show the UV-vis spectra of various graphene QDs in toluene.
Figure 21:
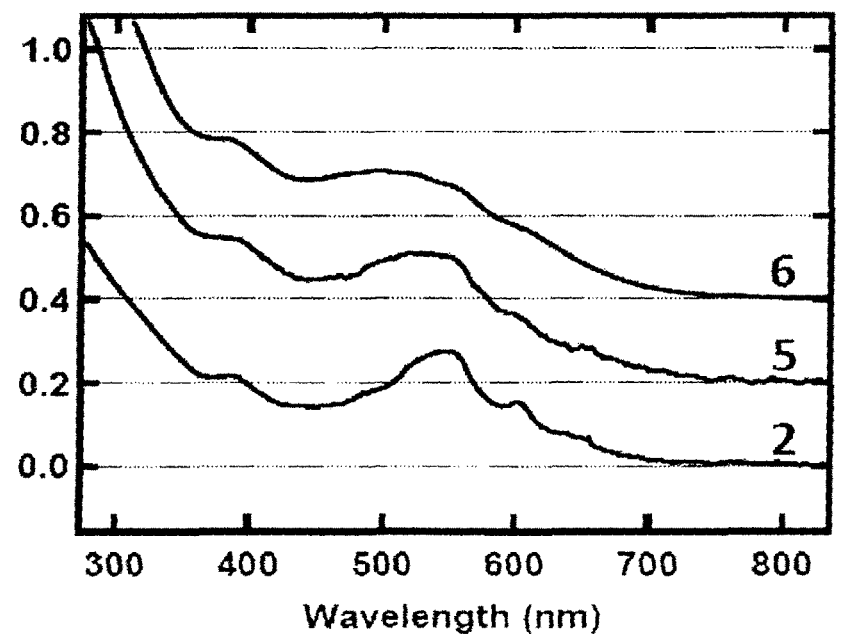

Optical Measurements. The gaps between the highest occupied molecular orbitals (HOMO) and the lowest unoccupied molecular orbitals (LUMO) of the graphene QDs 1-6 were determined with UV-vis absorption spectra (FIG. 20-21). Shown is the UV-vis spectra of graphene QDs 1-6 in toluene. 1, 3, and 4 have equal absorption edges at ~900 nm, and 2, 5, 6 at ~760 nm. In all cases the spectra appear continuous because of vibronic broadening and the small energy spacing between the excited electronic states. The HOMO-LUMO gaps were determined by the red edge of the absorption spectra, which for 1, 3, 4 are ~1.4 eV (~900 nm), and for 2, 5, 6 are ~1.6 eV (~760 nm). As expected, the QDs with 168 conjugated carbon atoms (1, 3, and 4) have smaller HOMO-LUMO gaps than those with 132 conjugated carbon atoms (2, 5, and 6) due to their larger size of conjugation. While the HOMO-LUMO gaps are dependent on the sizes of the graphene moieties, the effect of the covalent functionalization on the gaps is not significant. The functionalization only varies the relative intensities of the finer features that correspond to different absorption bands. This can be attributed to the change in the oscillator strengths of the electronic transitions due to the different electron distribution in the graphene moieties as well as the reduced molecular symmetry. In the spectrum of 6 the transition bands are not as distinct probably because of the existence of various isomers.

Photoelectron Spectroscopy Since the graphene QDs are extensions of polycyclic aromatic hydrocarbons, we anticipate that, as in other conjugated systems, covalently attaching electron-withdrawing or electron-donating groups should vary their redox potentials. In systems like conjugated polymers, it has been demonstrated that electron-donating groups generally raise the HOMO levels and electron-withdrawing groups lower the LUMO levels. This unique feature in the graphene QDs is of great importance for solar energy utilization, because it would allow us to tune energetics and thus dynamics of photo-induced charge injection independent of the bandgaps.

Figure 22:
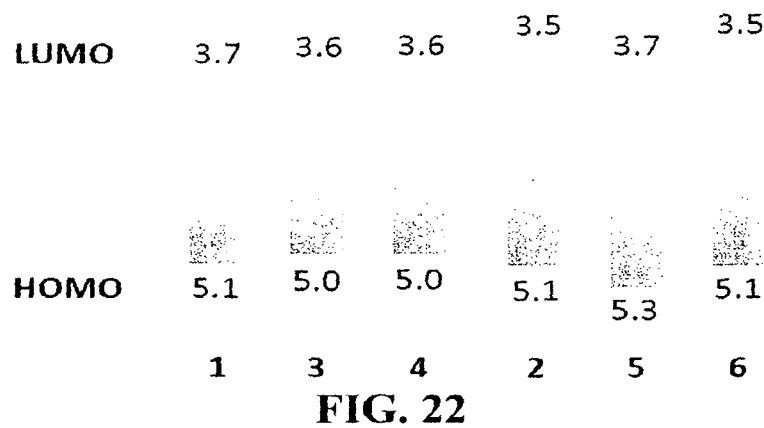
FIG. 22 shows the HOMO and LUMO levels of various QDs.

The HOMO levels of the graphene QDs were determined as the ionization threshold energy with ultraviolet (UV) photoelectron yield spectroscopy (PYS) in air, since our attempts with cyclic voltammetry of the QDs in solution were not successful. For the PYS measurements, a thin film (~50 nm thick) of the QDs was spin cast on an ITO-coated glass surface from a toluene solution. After it was completely dried it was mounted in the spectrometer. UV radiation from a deuterium lamp after going through a monochromator was focused on the film, and photoelectrons emitted from the film were detected with an open counter. With photon energy increased with an interval of 0.05 eV, the photoelectron counts were measured, leading to a photoelectron spectrum. The ionization threshold energy was determined from the onset of detected electrons, yielding the HOMO levels of the QDs below the vacuum level in electron volts. The LUMO levels of the QDs were subsequently determined from their HOMO levels and the HOMO-LUMO gaps determined with UV-vis absorption spectra (FIG. 20-21). The HOMO and LUMO levels of QDs 1-6 are summarized in FIG. 22.

It is apparent that covalent functionalization varies the energy levels of the graphene QDs without significantly changing their HOMO-LUMO gaps. Directly attaching the carboxylic acid group to the graphene moiety, as in the case of 5, has the most significant effect, lowering the HOMO levels of the QDs by 0.2 eV in comparison with the non-functionalized 2. The HOMO levels of both 3 and 4 were determined to be 5.0 eV below vacuum, 0.1 eV higher than that of the non-functionalized 1. Since 3 has electron-withdrawing groups and 4 electron-donating ones, the equal HOMO levels of the two suggests that the intermediate phenyl group between the functional groups and the graphenes reduces the effects of the functional groups. This is consistent with the HOMO level of 6, which, despite the present of multiple methoxy groups, has the same value as the non-functionalized QD 2. Electron-donating groups such as methoxy or amine groups have not been successfully directly attached to the graphene moieties, because of formation of quinones or radical cations at the nitrogen centers, as have been observed in smaller conjugated systems such as hexa-peri-hexabenzocoronene derivatives.

The effects of impurities in the QDs on the energy level determination are discussed below. From MALDI-MS it is apparent that the most likely impurities present are chlorinated byproducts or partially oxidized ones (FIG. 1). Because of the electron-withdrawing nature of the chlorine atoms, it is believed that the chlorinated products have lower HOMO levels, and therefore would not interfere with the determination of the HOMO levels from the low-energy edges in the PYS. Similarly, partially oxidized products have larger bandgaps and lower HOMO levels as well. Therefore, the determination of the HOMO and LUMO levels from the edges of the PYS and UV-vis spectra, respectively, has an effect of spectral selection, as the spectroscopic methods widely used in studying QDs of other semiconductors where a finite size inhomogeneity is always present.

Dye-Sensitized Solar Cells Dye-sensitized solar cells (DSSCs) were fabricated with previously reported methods (Barbe et al. J. Am. Ceram. Soc. 1997, 80, 3157-3171; Nazeeruddin et al. J. Am. Chem. Soc. 1993, 115, 6382-6390, incorporated herein by reference in their entirety, with graphene QDs as the sensitizers. The $TiO_2$ nanocrystalline thin films (~10 µm thick) on ITO glass were immersed in a solution of graphene QDs in a toluene/ethanol mixture (50/50, v/v) at 50° C. for various lengths of time. Because of the carboxylic acid groups present, QDs 14 and 5 can stain the $TiO_2$ nanocrystalline much more efficiently than 1 and 2, and thus we used staining time of 24 hours for 14 and 5 and 72 hours for 1 and 2. The electrolyte solution used for all the devices was 0.15M $I_2$, 0.015M $I_2$ in $CH_3CN$. For comparison, we also made DSSCs with a ruthenium complex N719 with the same conditions. The current-voltage characteristics of photovoltaic devices was measured with a 1000 W Xenon lamp (ozone free, Newport) with an AM 1.5 Global filter (Newport). The light intensity was calibrated with a NREL-traceable reference cell (Newport) to be 1 sun.

Figure 23:
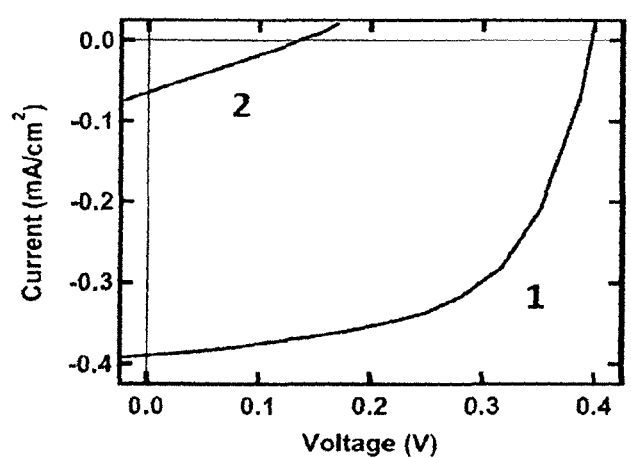
FIG. 23-24 show current-voltage (I-V) characteristics of typical dye-sensitized solar cells under a simulated AM 1.5 Global light source when various QDs were used as sensitizers.
Figure 24:
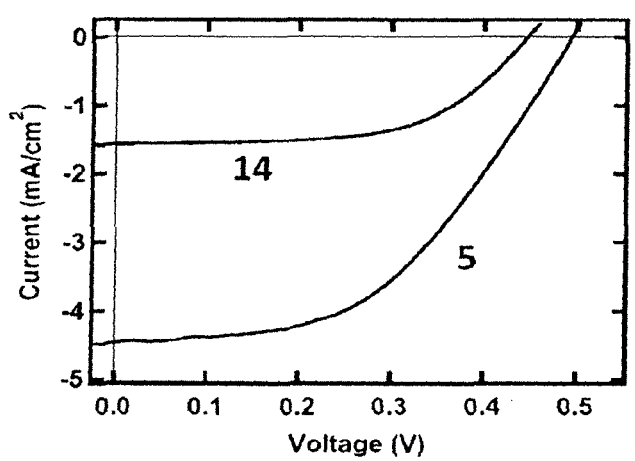

FIG. 23-24 show the current-voltage (I-V) characteristics of typical DSSCs under a simulated AM 1.5 Global light source when QDs 1, 2, 5, and 14 were used as sensitizers, respectively. The results obtained, including short-circuit current ($I_{sc}$), open-circuit voltage (Voc), fill factor (FF), maximum power ($P_{max}$), and energy conversion efficiency (η) are summarized in Table 1. The DSSCs based on functionalized graphene QDs 14 and 5 showed significantly better performances than the non-functionalized QDs, consistent with the effects of the acid groups that improve not only the binding affinity of the QDs with $TiO_2$ surfaces but also the photo-induced charge injection, confirming the importance of the linker groups in the graphene QD systems for photo-induced charge transfer processes.

Despite its broader absorption spectrum, QD 14 leads to lower overall efficiency than 5. This may be attributed to the presence of the phenyl group between the carboxylic acid groups and the graphene moiety, which could reduce the electronic coupling between the graphene and the $TiO_2$ films as in organic donor-bridge-acceptor systems. Meanwhile the orientation of the QDs on the $TiO_2$ surface may also play an important role. The carboxylic acid group in 5 is more accessible than those in 14 to the oxide surfaces and thus may make the graphene QDs orient vertically to the oxide surfaces. In 14, however, two of the three bulky solubilizing groups extend toward the carboxylic acid groups at a 60° angle and thus can shield the carboxylic acid groups from the oxide surfaces, so that the QDs are likely to adopt a non-vertical orientation. The molecular orientation not only determines the surface coverage of the QDs on $TiO_2$ surfaces, but also may affect the charge transfer dynamics because of the anisotropic electron distribution in the graphene QDs. Table 1 shows the characteristics of the DSSCs sensitized by graphene QDs 1, 14, 2, 5 and ruthenium complex N719. The electrolyte solution used for all the devices was 0.15M LiI, 0.015M $I_2$ in $CH_3CN$.

TABLE 1

|  | $I_{sc}$ (mA/cm$^2$) | $V_{oc}$ (V) | $P_{max}$ (mW/cm$^2$) | FF | $\eta$ (%) |
| --- | --- | --- | --- | --- | --- |
| 1 | 0.39 | 0.40 | 0.09 | 0.57 | 0.09 |
| 14 | 1.57 | 0.45 | 0.41 | 0.58 | 0.41 |
| 2 | 0.06 | 0.14 | 0.002 | 0.24 | 0.002 |
| 5 | 4.50 | 0.50 | 1.07 | 0.48 | 1.07 |
| N719 | 12.0 | 0.73 | 4.53 | 0.52 | 4.53 |

Among the QDs investigated the DSSCs based on QD 5 have by far the best performance, with a short-circuit current of 4.50 mA/cm$^2$, an open-circuit voltage of 0.50V and a fill factor of 0.48. The energy conversion efficiency is 1.07%, which however is still significantly lower than the DSSCs sensitized by the ruthenium complex N719 ($\eta$=4.53% in our studies). The unexpected low efficiency may be due to the formation of charge-transfer complexes between the graphene QDs with $I_2$, which is a common phenomenon for polycyclic aromatic hydrocarbons.

Materials. All starting materials were purchased either from Sigma Aldrich or Alfa Chemicals, and were used without further purification. All solvents, including NMR solvents, were used as received. Reactions were monitored by thin-layer chromatography (TLC) carried on silica gel plates (F-254, 250 μm, Dynamic Absorbents, Inc.). Silica gel (particle size 0.032-0.063 mm) from Dynamic Absorbents, Inc. was used for flash column chromatography.

Spectroscopy. All NMR spectra were recorded on a Varian 400 MHz or 500 MHz spectrometers. Chemical shifts are referenced internally to the solvent signal. All UV-vis absorption spectra were obtained on an Aegilent 8350 spectrometer. Matrix-assisted laser desorption/ionization (MALDI) reflectron time-of-flight (MALDI-TOF) technique was used for mass analysis of the compounds, and recorded on a Bruker Biflex III spectrometer. Tetracyanoquinodimethane (TCNQ) was used as the matrix for the analysis of the graphene quantum dots. The HOMO levels of graphene quantum dots were measured with ultraviolet (UV) photoelectron yield spectroscopy (Photo-Electron Spectroscopy in Air, Model AC-3, Riken Keiki Co., Ltd).

Fabrication and Characterization of Dye-Sensitized Solar Cells. TiO$_2$ nanocrystalline thin films (Degussa P25, ∞10 μm thick) were screen-printed on Fluorine-doped tin oxide (FTO) glass and sintered at 450° C. for 30 minutes, followed by the post-treatment with TiCl$_4$ solution.[25] Then they were stained in a solution of graphene quantum dots in a toluene/ethanol mixture (50/50, v/v) at 50° C. for 1-3 days. The areas of working devices range from 0.5 to 1.0 cm$^2$. Dye-sensitized solar cells were fabricated with previously reported methods with platinum as counter electrodes. The electrolyte solution used in all the devices was 0.15M LiI, 0.015M I$_2$ in CH$_3$CN. The current-voltage characteristics of photovoltaic devices was measured with a 1000 W Xenon lamp (ozone free, Newport) with an AM 1.5 Global filter (Newport). The light intensity was calibrated with a NREL-traceable reference cell (Newport) to be 1 sun.

While the invention has been illustrated and described in detail in the foregoing description, such an illustration and description is to be considered as exemplary and not restrictive in character, it being understood that only the illustrative embodiments have been described and that all changes and modifications that come within the spirit of the invention are desired to be protected. Those of ordinary skill in the art may readily devise their own implementations that incorporate one or more of the features described herein, and thus fall within the spirit and scope of the present invention.

What is claimed is:

1. A composition comprising a population of graphene quantum dots, wherein a quantum dot comprises graphene, a first solubilizing group, and a first binding group, wherein the first solubilizing group is a substituted phenyl moiety, wherein the substituted phenyl moiety is directly bonded to the graphene, wherein the substituted phenyl moiety comprises a substituent attached ortho- to the graphene.

2. The composition of claim 1, wherein the graphene includes from about 100 to about 60000 conjugated atoms.

3. The composition of claim 2, wherein the graphene has a ribbon structure having a monolayer thickness, a ribbon length, and a ribbon width, wherein the ribbon length is from about 2 nanometers to about 2 centimeters and the ribbon width is from about 0.5 nanometers to about 5 nanometers.

4. The composition of claim 2, wherein the conjugated atoms include
    (a) covalently-linked carbon atoms, and
    (b) a system of p-orbitals populated with delocalized electrons, wherein the system of p-orbitals overlap with one another across an intervening sigma bond to bridge the sigma bond, and the delocalized electrons are associated collectively to the graphene.

5. The composition of claim 1, wherein the graphene includes from about 100 to about 600 conjugated atoms.

6. The composition of claim 5, wherein the graphene has a sheet structure having a monolayer thickness, a sheet length, and a sheet width, wherein the sheet length is between about 1 nanometer and about 4 nanometers and the sheet width is from about 0.5 nanometers to about 5 nanometers.

7. The composition of claim 6, wherein the sheet width and the sheet length provide a sheet area of 3 square nanometers to about 20 square nanometers.

8. The composition of claim 1, wherein the first solubilizing group includes a steric hindering group.

9. The composition of claim 8, wherein the steric hindering group includes one branching group and three bulking groups.

10. The composition of claim 1, wherein the first binding group is a chemical functional group having an attraction to an inorganic solid.

11. The composition of claim 1, wherein the first binding group is a chemical functional group having an attraction to titanium dioxide.

12. The composition of claim 1, wherein the first binding group is
    a carbonyl or derivative thereof,
    a carboxylate or derivative thereof,
    a sulfonyl or derivative thereof,
    a phosphinyl or derivative thereof,
    a phosphonyl or derivative thereof,
    a phosphate or derivative thereof, or
    an arsenate or a derivative thereof.

* * * * *